US007205387B2

(12) United States Patent
Wang et al.

(10) Patent No.: US 7,205,387 B2
(45) Date of Patent: Apr. 17, 2007

(54) RECOMBINANT POLYPEPTIDE USEFUL FOR NEUROTROPHIN RECEPTOR MEDIATED GENE DELIVERY AND AS NEUROTROPHIN AGONIST

(75) Inventors: Shu Wang, Singapore (SG); Shan Shan Wu, Cambridge, MA (US); Jieming Zeng, Singapore (SG); Nan Ma, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 251 days.

(21) Appl. No.: 10/652,295

(22) Filed: Aug. 28, 2003

(65) Prior Publication Data

US 2005/0048606 A1    Mar. 3, 2005

(51) Int. Cl.
*C07K 14/00* (2006.01)
*C07K 5/00* (2006.01)

(52) U.S. Cl. ...................... 530/350; 530/300
(58) Field of Classification Search ............ None
See application file for complete search history.

(56) References Cited

U.S. PATENT DOCUMENTS

| | | | |
|---|---|---|---|
| 5,166,320 A | 11/1992 | Wu et al. | 530/395 |
| 5,169,764 A | 12/1992 | Shooter et al. | 435/69.7 |
| 5,512,661 A | 4/1996 | Shooter et al. | 530/399 |
| 5,958,875 A | 9/1999 | Longo et al. | 514/11 |
| 6,029,114 A | 2/2000 | Shamovsky et al. | 702/22 |
| 6,113,947 A | 9/2000 | Cleland et al. | 424/489 |
| 6,191,257 B1 | 2/2001 | Ledley et al. | 530/350 |
| 6,333,396 B1 | 12/2001 | Filpula et al. | 530/387.3 |
| 6,498,233 B1 | 12/2002 | Wels et al. | 530/350 |
| 6,602,993 B2 | 8/2003 | Wallach et al. | |

OTHER PUBLICATIONS

Pawson et al. 2003, Science 300:445-452.*
Varga et al. Biotechnol. Bioeng. 2000. 70: 593-605.*
Burgess et al. J of Cell Bio. 111:2129-2138, 1990.*
Bowie et al. Science, 1990, 247:1306-1310.*
Abdallah B et al., A powerful nonviral vector for in vivo gene transfer into the adult mammalian brain: polyethylenimine. Hum Gene Ther. 1996, 7: 1947-1954.
Beglove N et al., Design and Solution Structure of Functional Peptide Mimetics of Nerve Growth Factor J Med Chem., 43: 3530-3540, 2000.
Berkner KL, Development of adenovirus vectors for the expression of heterologous genes. Biotechniques 6: 616-629, 1988.

(Continued)

*Primary Examiner*—Janet L. Andres
*Assistant Examiner*—Chang-Yu Wang
(74) *Attorney, Agent, or Firm*—Klarquist Sparkman, LLP

(57) ABSTRACT

The invention provides a novel recombinant polypeptide that comprises a nucleic acid binding element and a hairpin motif that selectively binds to a neurotrophin receptor. The recombinant polypeptide may be used for neurotrophin receptor mediated delivery of nucleic acid, including therapeutic DNA, bound to the recombinant polypeptide. In one embodiment, the hairpin motif is a hairpin motif of a neurotrophin, such as nerve growth factor, brain derived neurotrophic factor, neurotrophin 3 and neurotrophin 4/5. The hairpin motif is also a neurotrophin agonist and therefore may be used to treat any disorder responsive to neurotrophin treatment, such as neurological disorders and tumour. In one embodiment the agonist comprises a hairpin motif that selectively binds to a neurotrophin receptor and a positively charged binding domain which is believed to enhance receptor binding by binding to negatively charged cell membrane.

17 Claims, 15 Drawing Sheets

NL4-10K/DNA

| nmol/µg: | 0 | 0.03 | 0.15 | 0.3 | 1.5 | 3 |
|---|---|---|---|---|---|---|
| N/P ratio: | 0 | 0.1 | 0.5 | 1 | 5 | 10 |

NL4/DNA

| nmol/µg: | 0 | 0.03 | 0.15 | 0.3 | 1.5 | 3 |
|---|---|---|---|---|---|---|

OTHER PUBLICATIONS

Boussif O et al., A versatile vector for gene and oligonucleotide transfer into cells in culture and in vivo: Polyethylenimine. Proc. Natl. Acad. Sci. USA, 1995; 92: 7297-7302.

Climent et al. Astrocytes in culture express the full-length Trk-B receptor and respond to brain derived neurotrophic factor by changing intracellular calcium levels: effect of ethanol exposure in rats. Neurosci. Letters 2000; 288: 53-56.

Cristiano RJ et al., Hepatic Gene Therapy: Adenovirus Enhancement of Receptor-Mediated Gene Delivery and Expression in Primary Hepatocytes. Proc. Natl. Acad. Sci. USA, 90: 2122-2126, 1993.

Davis ME, Non-viral gene delivery system; Current opinion in biotechnology 2002, 13: 128-131.

Fortunati E, et al., "A multi-domain protein for β1 integrin-targeted DNA delivery", Gene Therapy (2000) 7, 1505-15.

Goldman CK et al., Targeted gene delivery to Kaposi's sarcoma cells via the fibroblast growth factor receptor. Cancer Res, 57: 1447-1451, 1997.

Goula D, et al. Size, diffusibility and transfection performance of linear PEI/DNA complexes in the mouse central nervous system. Gene Therapy, 1998; 5:712-717.

Hoganson DK et al., Targeted Delivery of DNA Encoding Cytotoxic Proteins through High-Affinity Fibroblast Growth Factor Receptors Human Gene Therapy, 9: 2565-2575, 1998.

Ibanez CF et al., Neurotrophic factors: from structure-function studies to designing effective therapeutics TIBTECH, 13:217-227 1995.

Khadake JR and Rao MR, Condensation of DNA and Chromatin by an SPKK-Containing Octapeptide Repeat Motif Present in the C-Terminus of Histone H1. Biochemistry 36: 1041-1051, 1997.

Lee RJ and Huang L, Folate-targeted, Anionic Liposome-entrapped Polylysine-condensed DNA for Tumor Cell-specific Gene Transfer J. Biol. Chem., 271, 8481, 1996.

Li S and Huang L., Nonviral gene therapy: promises and challenges. Gene Therapy, 2000, 7: 31-34.

Meakin SO and Shooter EM, The nerve growth factor family of receptors. Trends Neurosci., 15: 323-331, 1992.

Medina-Kauwe LK, Kasahara N, Kedes L, 3PO, a novel nonviral gene delivery system using engineered Ad5 penton proteins, Gene Therapy (2001) S, 795-803.

Medina-Kauwe LK, Maguire M, Kasahara N, Kedes L, Nonviral gene delivery to human breast cancer cells by targeted Ad5 penton proteins, Gene Therapy (2001) 8, 1753-61.

Neet KE and Campenot RB, Receptor binding, internalization, and retrograde transport of neurotrophic factors. CMLS Cell. Mol. Life Sci., 58:1021-1035, 2001.

Niidome T and Huang L, Gene therapy progress and prospects: nonviral vectors. Gene Therapy, 2002, 9:1647-1652.

Remy JS et al., Targeted Gene Transfer into Hepatoma Cells with Lipopolyamine-Condensed DNA Particles Presenting Galactose Ligands: A Stage Toward Artificial Viruses. Proc. Natl. Acad. Sci. USA, 92:1744, 1995.

Saragovi HU and Gehring K, Development of pharmacological agents for targeting neurotrophins and their receptors. TiPS, 21:93-98, 2000.

Sakris.C. et al., Efficient transduction of neural cells in vitro and in vivo by a baculovirus-derived vector Proc. Natl. Acad. Sci. USA, 97: 14638-14643 2000.

Schaffer and Lauffenburger, Optimization of Cell Surface Binding Enhances Efficiency and Specificity of Molecular Conjugate Gene Delivery. J Bio Chem, 273: 28004-28009, 1998.

Shimizu N et al., Biological activity of brain-derived neurotrophic factor with mismatched disulfide linkages produced by *Escherichia coli* .Biosci. Biotech. Biochem., 60: 971-974, 1996.

Sofroniary et al., Nerve growth Factor signaling, neuroprotection, and neural repair . Annu. Rev. Neurosci. 2001; 24: 1217.

Thorne RG and Frey II WH, Delivery of neurotrophic factors to the central nervous system: pharmacokinetic considerations. Clin Pharmacokinet, 40:907-946, 2001.

Wager E, et al., Transferrin-Polycation-DNA Complexes: The Effect of Polycations on the Structure of the Complex and DNA Delivery to Cells. Proc. Natl. Acad. Sci. USA, 88: 4255-4259, 1991.

Wiesmann C et al., Crystal structure of nerve growth factor in complex with the ligand-binding domain of the TrkA receptor. Nature, 401: 184-188, 1999.

Wu GY and Wu CH, Receptor-mediated in vitro gene transformation by a soluble DNA carrier system J Biol Chem., 262:4429-32, 1987.

Xie Y et al., Nerve Growth Factor (NGF) Loop 4 Dimeric Mimetics Activate ERK and AKT and Promote NGF-like Neurotrophic Effects. J Bio. Chem, 275: 29868-29874, 2000.

Zenke M et al., Receptor-Mediated Endocytosis of Transferrin-Polycation Conjugates: An Efficient Way to Introduce DNA Into Hematopoietic Cells. Proc. Natl. Acad. Sci. USA, 87: 3655-3659, 1990.

Krüttgen et al., The Role of the Nerve Growth Factor Carboxyl Terminus in Receptor Binding and Conformational Stability. J. Bio. Chem, 272: 29222-29228, 1997.

Leopold L. Itag et al., Role of Variable β-Hairpin Loop in Determining Biological Specificities in Neurotrophin Family. J. Bio. Chem, 269: 19941-19946, 1994.

Mikael Rydén et al., Binding of Neurotrophin-3 to $p75^{LNGFR}$, TrkA, and TrkB Mediated by a Single Functional Epitope Distinct From That Recognized by TrkX. J. Bio. Chem, 271:5623-5627, 1996.

Lynne LeSateur et al., Small Peptide Mimics of Nerve Growth Bind TrkA Receptors and Affect Biological Reponses. J. Bio. Chem, 270: 6564-6569.

Sang B. Woo et al., Characterization of Histidine Residues Essential for Receptor Binding and Activity of Nerve Growth Factor. J. Bio. Chem, 271:24433-2441, 1996.

Carlos F. Ibanez et al., Disruption of the Low Affinity Receptor-Binding Site in NGF Allows Neuronal Survival and Differentiation by Binding to the trk Gene Product. Cell, vol. 69:329-41, Apr. 17, 1992.

Mikael Ryden et al., Functional analysis of mutant neurotrophins deficient in low-affinity binding reveals a role for $p75^{LNGFR}$ in NT-4 signalling, The EMBO Journal, vol. 14, No. 9, pp. 1979-1990, 1995.

Igor L. Shamovsky et al., The interaction of neurotrophins with $p75^{NTR}$ common neurotrophin receptor: A comprehensive molecular modeling study. Protein Science (1999), 8:2223-2233.

O'Leary, P., et al. 2003. Design of potent peptide mimetics of brain-derived neurotrophic factor. *The Journal of Biological Chemistry* 278(28):25738-25744.

Pollack, S.J. et al. 2002. Small molecule Trk receptor agonists and other neurotrophic factor mimetics. Current Drug Targets. CNS Neurological Disorders. 1(1):59-80. Citation obtained from the following URL: http://www.bentham-science.org/old-sample/cdtcnsnd1-1/pollack/pollack-ms.htm.

Zeng, J. et al. 2005. Enhanced gene delivery to PC12 cells by a cationic polypeptide. *Biomaterials*. 26:679-686.

Ma, N. et al. 2004. Nerve growth factor receptor-mediated gene transfer. *Molecular Therapy*. 9(2):270-281.

\* cited by examiner

A.

B.

C.

A.

B.

A. TrkA

B. Erk

C. Erk+K252a

A.

B.

C.

RECOMBINANT POLYPEPTIDE USEFUL FOR NEUROTROPHIN RECEPTOR MEDIATED GENE DELIVERY AND AS NEUROTROPHIN AGONIST

FIELD OF INVENTION

The invention relates to a recombinant polypeptide useful in targeted gene delivery, in particular neurotrophin receptor mediated gene delivery and useful as neurotrophin agonist, and its preparation.

BACKGROUND OF INVENTION

Targeted gene delivery to selected cell types provides a means for highly specific gene expression. Improved efficiency of gene transfer could be achieved through enhancing the entry of gene vectors into the desired cells and reducing the uptake of the vectors by non-target cells. For a therapeutic application, targeted gene delivery is critical in ensuring therapeutic effects in the cells of interest while limiting side effects, including immune, inflammatory and cytotoxic responses, caused by the expression of exogenous genes in non-target cells.

One approach for targeted gene delivery is to use ligand-associated delivery vectors. Via the ligands, the vectors recognize and bind to cell surface receptors that are unique to the target cells and that may undergo endocytosis upon binding to the ligands. The receptor-vector complexes, together with the surrounding plasma-membrane, may therefore become intracellular transport vesicles. Following gene escape from the vesicles and translocation of the gene to the nucleus, the gene product can be expressed. This receptor-mediated intracellular gene delivery was first reported by Wu G Y and Wu C H in 1987 (Receptor-mediated in vitro gene transformation by a soluble DNA carrier system. J Biol Chem 1987 Apr. 5; 262:4429–32; U.S. Pat. No. 5,166,320, granted Nov. 24, 1992) and has since received great attention in the field of drug/gene delivery. Many ligand-receptor systems have been investigated to date for targeted gene delivery. The ligands tested include asialoglycoproteins (Wu G Y and Wu C H, J Biol Chem., 262:4429–32, 1987), integrin-binding peptides (Berkner K L, Biotechniques 6: 616–629, 1988; Cristiano R J et al., Proc. Natl. Acad. Sci. USA, 90: 2122–2126,1993), transferrin (Zenke M et al., Proc. Natl. Acad. Sci. USA, 87: 3655–3659,1990; Wanger E, et al., Proc. Natl. Acad. Sci. USA, 88: 4255–4259,1991; U.S. Pat. No. 5,922,859), galactose (Remy J S et al., Proc. Natl. Acad. Sci. USA, 92:1744, 1995), folate (Lee R J and Huang L, J. Biol. Chem., 271, 8481, 1996), fibroblast growth factor (Goldman C K et al., Cancer Res, 57: 1447–1451, 1997; Hoganson D K et al., Human Gene Therapy, 9: 2565–2575, 1998), and epidermal growth factor (Schaffer and Lauffenburger, J Bio Chem, 273: 28004–28009, 1998). These ligands have been used to target mainly hepatocytes and tumor cells. The gene delivery systems based on the ligands are defined, in terms of their functions, by relatively well characterized ligand-receptor binding mechanisms involving related receptors. Very little has been established however for targeting gene vectors through receptor-ligand interaction to cells in a complex system, such as the nervous system.

Disorders in the nervous system, especially the central nervous system (CNS), such as stroke, epilepsy, head and spinal cord trauma, Parkinson's disease, Huntington's disease, Alzheimer's disease, amyotrophic lateral sclerosis, and many neurogenetic disorders, come with devastating effects on the individual and high social costs associated with chronic care and lost productivity. Many of the aforementioned disorders are related to the absence, malfunction or ineffectiveness of one gene or more and do not respond well to conventional therapeutic means. Gene transfer into the CNS has, therefore, been considered as a potential approach to treatment of these disorders. This approach may alter expression levels of neurotrophic factors, anti-apoptotic proteins, antioxidant molecules and other therapeutic factors to restore, halt or prevent the degeneration of cells in the CNS, especially neurons. Gene therapy also offers much hope for the treatment of CNS malignancies.

The unique characteristics of the CNS, the most sophisticated organ in the body, present several obstacles to successful gene therapy within the system. These characteristics include limited access to the CNS due to the physical barriers of the skull and the blood-brain barrier, the nature of terminally differentiated neurons and the difficulty of efficiently transfecting them with therapeutic genes. Moreover, the neuron types found within the CNS are very diverse, many of which are critical to physiological functions and highly sensitive to any kinds of changes. Under neurological situations, a disorder may affect one subtype of neurons and leave others unaffected. These features appeal strongly for the development of CNS gene therapy that restricts the expression of a therapeutic gene to a particular type of CNS cell, thus limiting possible side effects caused by gene expression in non-target CNS cells.

Currently, targeted gene delivery in the CNS is achieved simply through direct stereotactic injection of naked DNA or gene transfer vectors into well-defined anatomical locations, which may transduce various types of cells around the injection site. Retrograde axonal transport of viral or non-viral gene vectors offers another way to target neurons in different regions by choosing a proper injection site either in the CNS or the periphery. The method, however, transduce all projection neurons and does not distinguish subtypes of neurons.

Neurons are well known for their difference in the chemical transmitters that they use to deliver signals and in the receptors that they use to receive the signals. The nervous system makes use of 9 small-molecule transmitters and more than 50 neuroactive peptides, providing a way for classifying neurons based on their neurotransmitter phenotypes. In addition to their difference in sensitivities to various neurotransmitters, different neurons may also respond differently to another type of molecules called neurotrophic factors. These trophic factors are endogenous, soluble polypeptides displaying profound effects on the development, growth and survival of neurons and are believed to have great potential in the treatment of neurological disorders and CNS traumatic injuries. Among more than 20 known neurotrophic factors, the best-studied group is the neurotrophins, a family of structurally and functionally related polypeptides about 120 amino acids in length and sharing about 50% amino acid sequence identity. Four major neurotrophins isolated from mammals are nerve growth factor (NGF) (see SEQ ID NO:1 for human NGF sequence), brain-derived neurotrophic factor (BDNF) (see SEQ ID NO:2 for human BDNF sequence), neurotrophin 3 (NT3) (see SEQ ID NO:3 for human NT3 sequence) and neurotrophin 4/5 (NT4/5) (see SEQ ID NO:4 for human NT4/5 sequence). The neurotrophins are synthesized and secreted from neuronal target cells as non-covalently bound homodimers and act through retrograde signaling after binding to their nerve terminal-localized receptors. There are two main classes of receptors for the neurotrophins: the receptor protein tyrosine kinases including TrkA, TrkB and TrkC, and a 75-kDa transmembrane glycoprotein, p75$^{NTR}$. NGF interacts selectively with TrkA, BDNF and NT4/5 primarily with TrkB and NT3 mainly with TrkC and, to a lesser extent, also with TrkA and TrkB (Meakin S O and Shooter E M, Trends Neurosci., 15: 323–331, 1992). All the neurotrophins interact with p75$^{NTR}$, but with relatively low affinity as compared with their interaction with Trks.

Immunostaining reveals that Trks are expressed moderately in neurons and weakly in astrocytes in the adult human brain. No Trk staining is identified in oligodendrocytes. p75$^{NTR}$ is present in neurons, especially during development, in oligodendrocytes and at very low levels in many mature astrocytes. As a consequence of the Trk and p75$^{NTR}$ expression in various types of neurons, neurotrophins affect both overlapping and distinct subgroups of neurons (Thorne R G and Frey II W H, Clin Pharmacokinet, 40:907–946, 2001). Basal forebrain-cholinergic neurons respond to all four neurotrophins. Other neurons responsive to NGF include the striatal-cholinergic neurons, sympathetic sensory neurons, and neural crest-derived small-fibre sensory neurons. Other neurons responsive to BDNF include midbrain-dopaminergic neurons, spinal cord motor neurons, striatal-GABAergic and neural crest-derived medium-fibre sensory neurons and retinal ganglion cells. Other responsive neurons to NT3 include locus ceruleus neurons, midbrain-dopaminergic neurons, striatal-GABAergic neurons, sympathetic sensory neurons, and neural crest-derived large-fibre sensory neurons. The neurons responsive to NT4/5 also include locus ceruleus neurons, midbrain-dopaminergic neurons, striatal-GABAergic neurons, sympathetic and neural crest-derived sensory neurons, motor neurons and retinal ganglion cells. Outside the nervous system, NGF and TrkA expression is detected in B lymphocytes, T lymphocytes, mast cells, monocytes and macrophages, suggesting a role for NGF in immune and inflammatory functions. In addition, human tumor tissues up-regulate neurotrophin receptors and are responsive to NGF (Saragovi H U and Gehring K, TiPS, 21: 93–98, 2000).

Since the receptor-mediated endocytosis and retrograde transport of the ligand-receptor complexes are essential to neurotrophin signaling within the aforementioned cells (Neet K E and Campenot R B, CMLS Cell. Mol. Life Sci., 58:1021–1035, 2001), these polypeptides are candidates for targeting ligands that can be used to target gene vectors to Trk or p75$^{NTR}$ positive cells. For example, native neurotrophin polypeptides can be chemically conjugated to a cationic lipid or polymer that has the capability to bind to and condense DNA. This procedure, however, requires relatively larger amounts of purified polypeptides and may involve harsh chemical reactions that may significantly reduce bioactivities of the polypeptides. Recombinant DNA technology is one of the common methods used to produce biologically active, full-length neurotrophin polypeptides, as described in U.S. Pat. No. 5,606,031 and U.S. Pat. No. 6,005,081. Using these techniques in a bacterial expression system, misfolded variants of neurotrophins, differing from their authentic forms by the incorrect pairing of their cysteine residues, constitute a major problem. Neurotrophin polypeptides have similar structures that contain cystine knot motifs, with six residues of cysteine at highly conserved positions. The formation of correctly paired intramolecular disulfide bonds is required for full biological activity of a neurotrophin. A study using *E. Coli* to express BDNF has reported ten protein variants with incorrectly-paired disulfide linkages among six residues of cysteine, and all of them had much lower biological activity than that of native BDNF and may significantly inhibit the biological activity of authentic BDNF when used together (Shimizu N et al., Biosci. Biotech. Biochem., 60: 971–974, 1996). Other potential problems preventing the efficient use of a large protein as a targeting ligand include proteolytic degradation tendency, immunogenecity, and poor pharmacokinetics.

While all neurotrophins share almost the same core structure composed of a pair of two-stranded, twisted β-sheets, there are seven distinct regions in the proteins, including N terminus, loop regions I, II, III, β strand region IV, loop region V and C terminus, with higher than average sequence diversity (Ibanez C F, TIBTECH, 13: 217–227, 1995). Various approaches, from site-directed mutagenesis, deletion, chimeric molecule construction to crystal structure analysis, have been used to study structural determinants of neurotrophin effects. These studies have confirmed the amino acid residues that are important for binding to Trk receptors are localized, in the case of NGF, in N-terminal region (#1–8), loop region II (#40–49) and loop region V (#96–97) (Ibanez C F, TIBTECH, 13: 217–227, 1995). The study on the crystal structure of NGF in complex with the immunoglobulin-like domain 5 of TrkA (Wiesmann C et al., Nature, 401: 184–188, 1999) brought to attention on two patches; one patch involving the core beta-sheet of the homodimeric NGF molecule and another patch comprising the N-terminal residues of NGF for specific interaction with TrkA. Small peptide mimetics of NGF have been reported to activate TrkA-related signal transduction and promote NGF-like neurotrophic effects (U.S. Pat. No. 5,958,875; U.S. Pat. No. 6,017,878; Beglove N et al., J Med Chem., 43: 3530–3540, 2000; Maliartchouk S et al., J. Bio. Chem., 275: 9946–9956, 2000; Xie Y et al., J Bio. Chem, 275: 29868–29874, 2000). These peptide mimetics need to be cyclic, not only being sequence analogs but also structure analogs of NGF loops, in order to be biologically active.

SUMMARY OF INVENTION

In one aspect, the invention provides a recombinant polypeptide comprising a cell targeting element and a nucleic acid binding element wherein the cell targeting element is a hairpin motif that selectively binds to a neurotrophin receptor. In various embodiments, the polypeptide comprises a hairpin motif of a neurotrophin.

In another aspect, the invention provides a recombinant nucleic acid molecule encoding a recombinant polypeptide according to the invention. The invention also provides a composition comprising a nucleic acid and a recombinant polypeptide according to the invention.

The polypeptide according to the invention can be used for targeted delivery of nucleic acid, including DNA to cells that express a neurotrophin receptor and therefore can be advantageously used to treat neuronal disorders. The invention in different aspects therefore also provides a method of delivery of nucleic acid into a cell expressing a neurotrophin receptor comprising administering a composition of the invention, and a method of treating a neuronal disorder in a subject comprising administering to the subject a composition of the invention. The invention in other aspects provides the use of the polypeptide for delivery of nucleic acid into a cell expressing a neurotrophin receptor; to treat a neuronal disorder in a subject; and to prepare a medicament for the treatment of a neuronal disorder in a subject.

The invention in another aspect provides a neurotrophin agonist comprising a hairpin motif that selectively binds to a neurotrophin receptor. In various embodiments, the hairpin motif is a hairpin motif of a neurotrophin and the agonist may further advantageously comprise a positively charged domain, which may enhance the agonist activity. The agonist of the invention may be used to treat disorders responsive to neurotrophin treatment. The invention in other aspects therefore provides a composition comprising an agonist of the invention and a pharmaceutically acceptable carrier or diluent and methods of treating a disorder responsive to neurotrophin treatment in a subject comprising administering to the subject an effective amount of the agonist or a composition comprising an effective amount of the agonist. In other aspects, the invention provides use of an agonist of the invention to treat or to prepare a medicament for the treatment of a disorder responsive to neurotrophin treatment.

(A): NL4-10K was used to deliver pCAGluc plasmid DNA to PC12 cells. Short peptides, NL4, 10K, and a mixture of NL4 and 10K peptides (NL4 & 10K) were used as controls. Cells were transfected with complexes containing 1 μg of pCAGluc/well in a 24-well plate in the presence of 100 μM of chloroquine. Luciferase expression was assayed 24 h after the transfection. Results are expressed in relative light units (RLU)/mg protein±SE. **P<0.01 compared to controls.

(B): Competitive inhibition of NL4-10K-mediated gene delivery into PC12 by NGF. PC12 cells were transfected, in the presence of 100 μM of chloroquine, with NL4-10K/pCAGluc complexes prepared with a peptide/DNA (nmol/μg) of 1.5 (N/P ratio of 5), with or without co-incubation with free NGF, NL4, 10K or NL4-10K. *P<0.05 and **P<0.01 compared to transfection without additives.

(C): NL4-10K mediates gene delivery into primary neurons and glial cells. Primary neurons and glial cells from the rat cortex were transfected with complexes containing 1 μg of pCAGluc/well in a 24-well plate in the presence of 100 μM of chloroquine. After 4 h, an equal volume of normal culture medium was added and incubated for 24 h before luciferase expression assay. **P<0.01 compared to the 10K controls.

Figure 1:
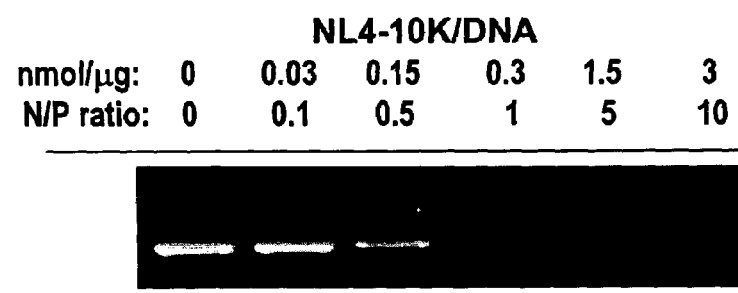
FIG. 1: NL4-10K, but not NL4, binds to plasmid DNA and retards its migration in agarose gel under electrophoresis.
Figure 1:
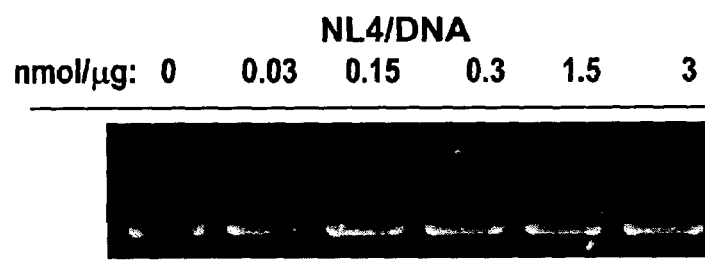
Figure 2:
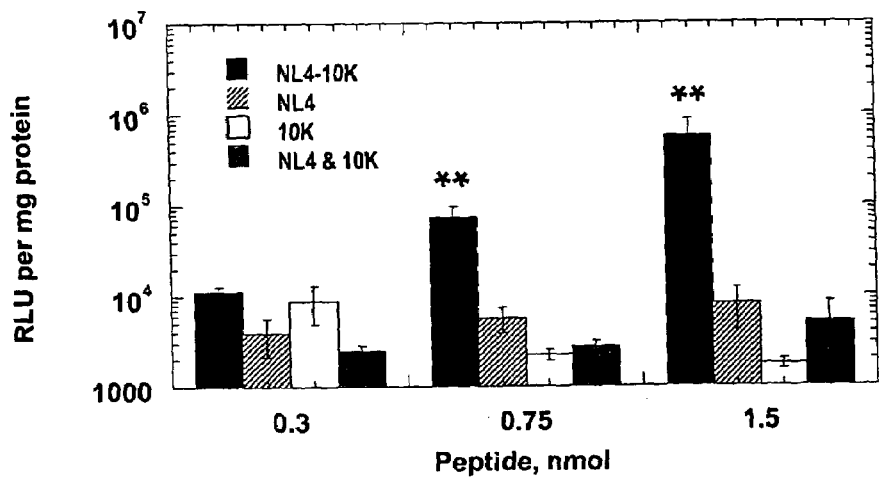
FIG. 2: NL4-10K mediates target-specific gene delivery in vitro.
Figure 2:
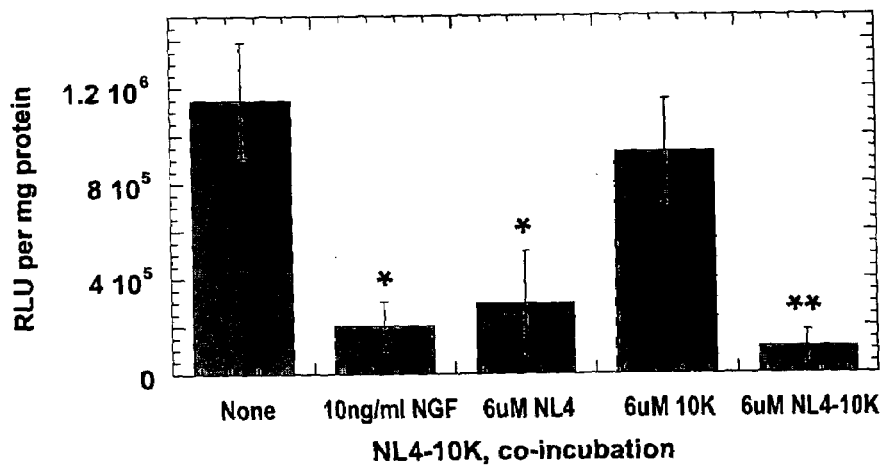
Figure 2:
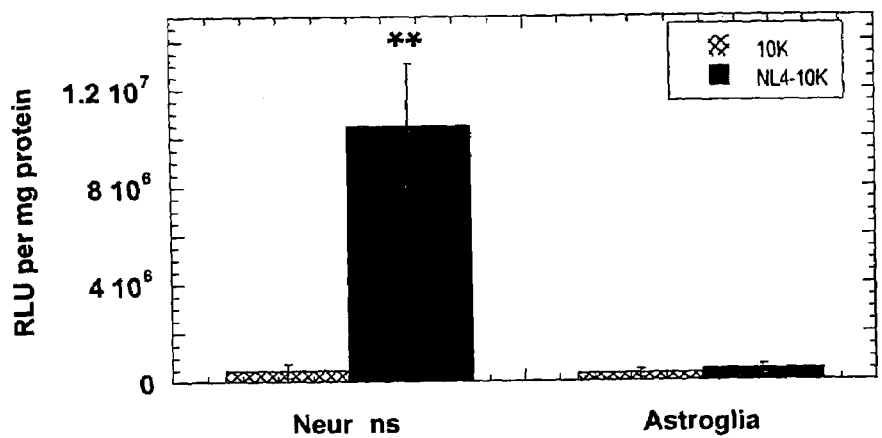
Figure 3:
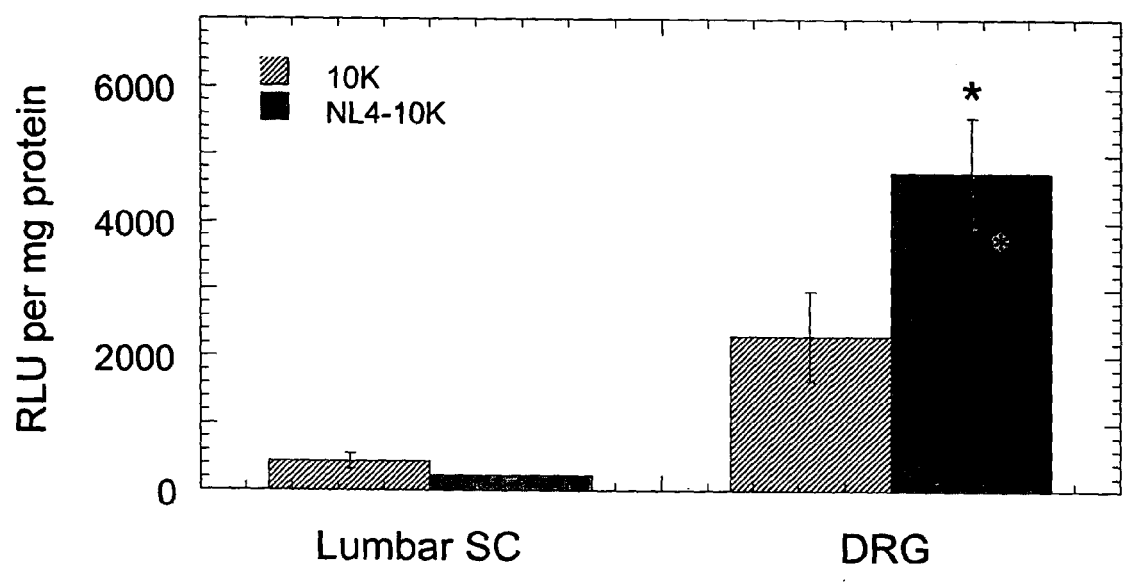

FIG. 3: NL4-10K mediated gene expression into dorsal root ganglia (DRG) in vivo. NL4-10K-containing triplexes were formed as described in the Examples. For all triplexes, the peptide/DNA (nmol/μg) ratio was 1.5 (N/P ratio of 5). Triplexes were administered intrathecally to rats under anesthesia. DRG were collected 3 days after injection. Results are expressed in relative light units (RLU)/mg protein±SE.

Figure 4:
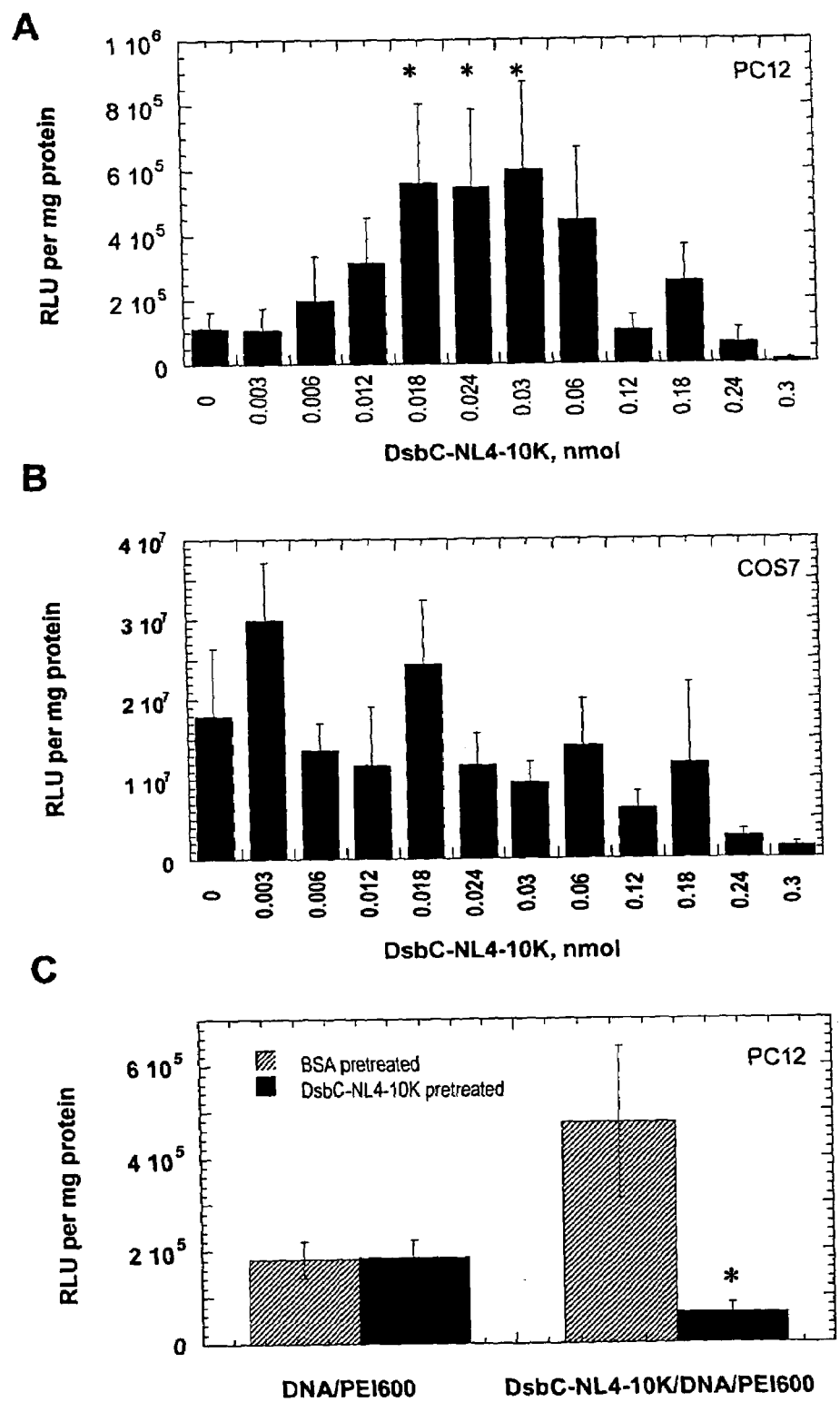

FIG. 4: Gene expression mediated by DsbC-NL4-10K.

(A) and (B): DsbC-NL4-10K/DNA/protamine triplexes were used to transfect PC12 (A) and COS7 (B) cells, respectively. To form the triplexes, DsbC-NL4-10K protein and pCAGluc plasmid (0.1 μg/well in 96-well plates) were incubated at various ratios at room temperature for 30 min in 20 μl Opti-MEM. After adding protamine (2 μg per μg DNA), the complexes were incubated for another 30 min. Results are expressed in relative light units (RLU)/mg protein±SE.

(C): Inhibition of DsbC-NL4-10K/DNA/PEI600-mediated gene delivery to PC12 cells by NL4-10K pretreatment. PC12 cells were pretreated with DsbC-NL4-10K or bovine serum albumin before transfection. To form DsbC-NL4-10K/DNA/PEI600 triplexes, DsbC-NL4-10K were added to DNA at protein/DNA (nmol/μg) ratio of 0.3 (N/P ratio of 1), after which PEI600 was added to the complexes at the N/P ratio of 20. Cells were exposed to 0.1 μg DNA per well in a 96-well plate. Results are expressed in relative light units (RLU)/mg protein±SE.

Figure 5:
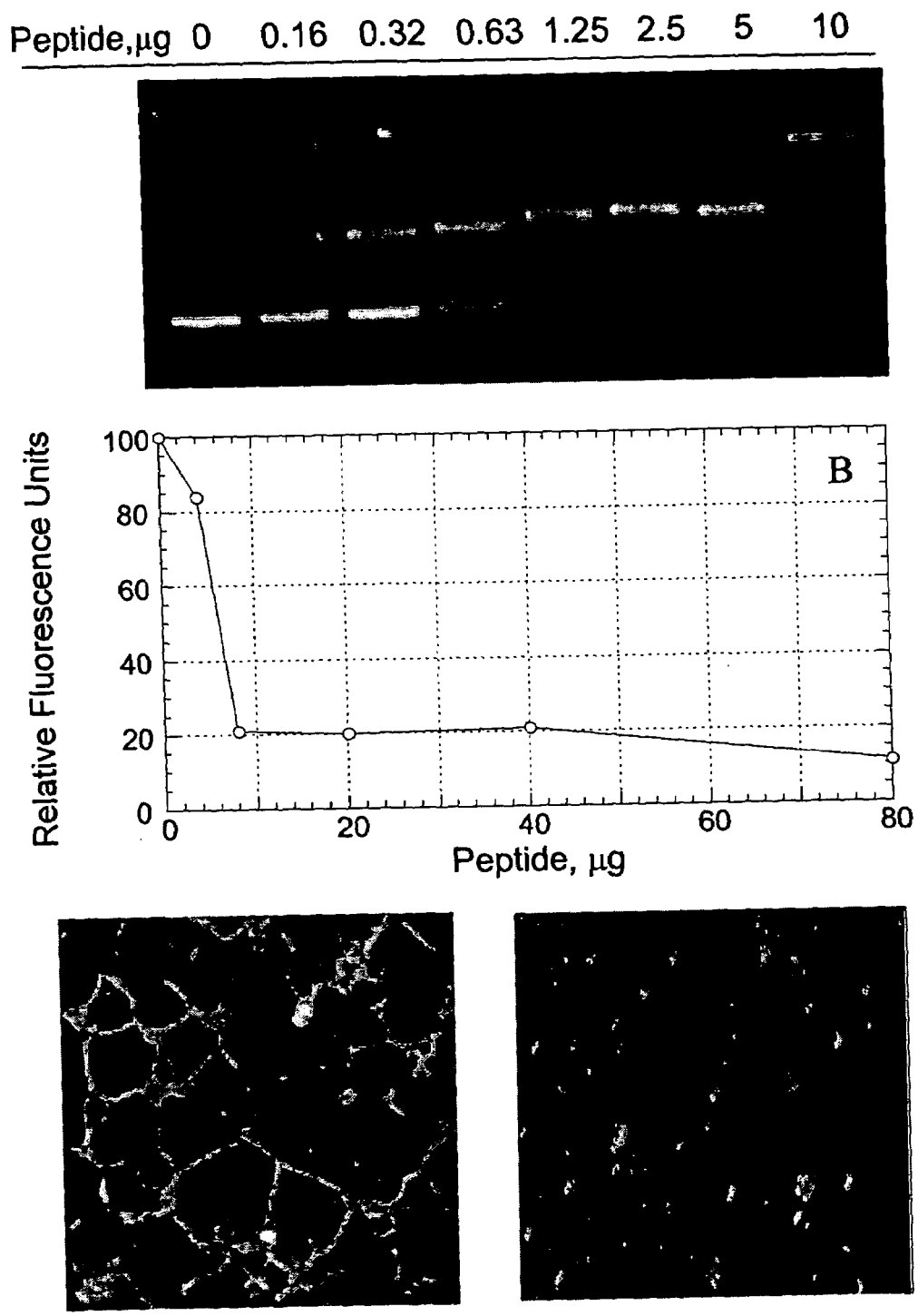

FIG. 5: $SPKR_4NL1-2$ binds to and condenses plasmid DNA.

(A): Electrophoretic mobility of plasmid DNA through a 1% agarose gel was reduced by $SPKR_4NL1-2$ binding. Various amounts of peptide were mixed with 0.1 μg of DNA in a volume of 20 μl for 30 min before electrophoresis.

(B): The fluorescence of ethidium bromide intercalated in DNA was reduced by the addition of $SPKR_4NL1-2$ that displaces ethidium bromide. The indicated amounts of peptide were added to 0.8 μg DNA pre-mixed with ethidium bromide.

Figure 6:
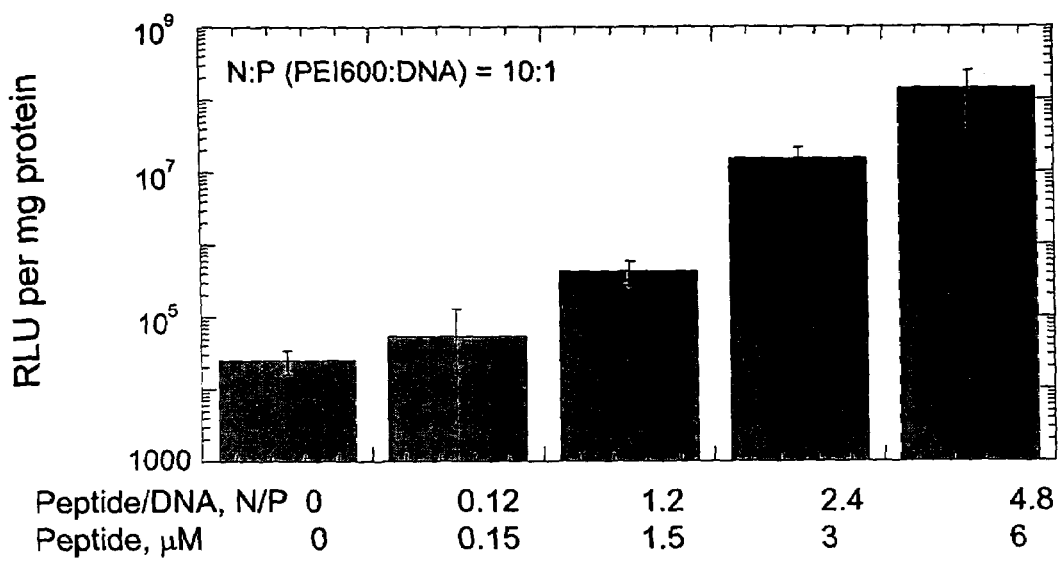
Figure 6:
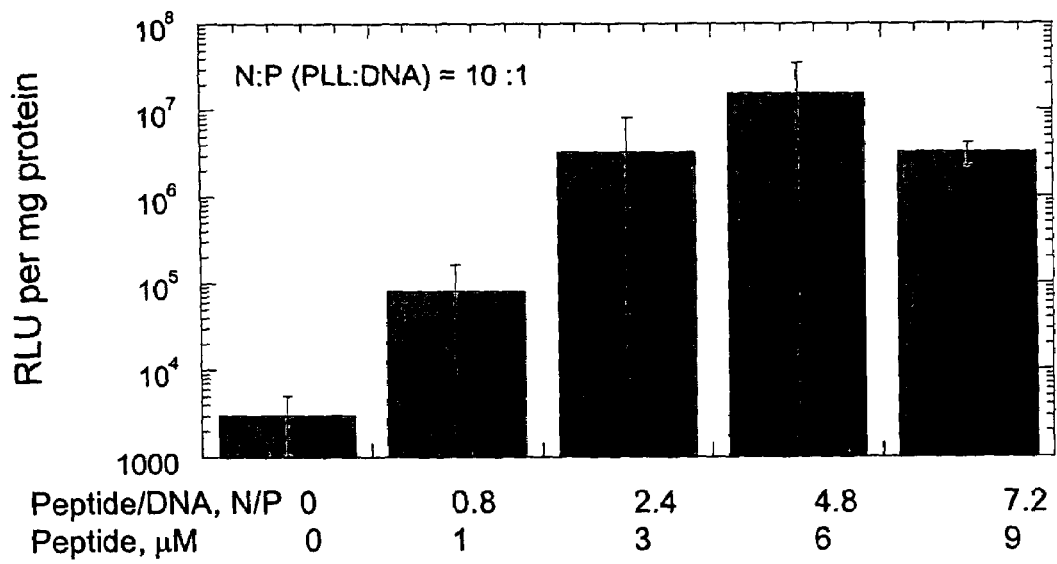

(C) & (D): Atomic force microscopy images of supercoiled plasmid DNA and $SPKR_4NL1-2$DNA/PEI600 complexes, respectively. The N/P ratios of peptide:DNA and PEI600:DNA were 2:1 and 10:1, respectively. Both images were collected as 4 $\mu m^2$ fields and the scale bar represents 0.5 μm FIG. 6: $SPKR_4NL1-2$ enhances polycation-mediated gene transfection of PC12 cells. To form complexes used for each well of a 48-well plate, 0.5 μg of pCAGluc plasmid was first mixed with varying amounts of the peptide and incubated for 30 min, after which polycation was added and the mixture incubated for a further 30 min. Luciferase activity is given in relative light units (RLU) per mg total protein. (A) PEI600 at an N/P ratio of 10. (B) Poly-L-lysine (PLL) at an N/P ratio of 10.

Figure 7:
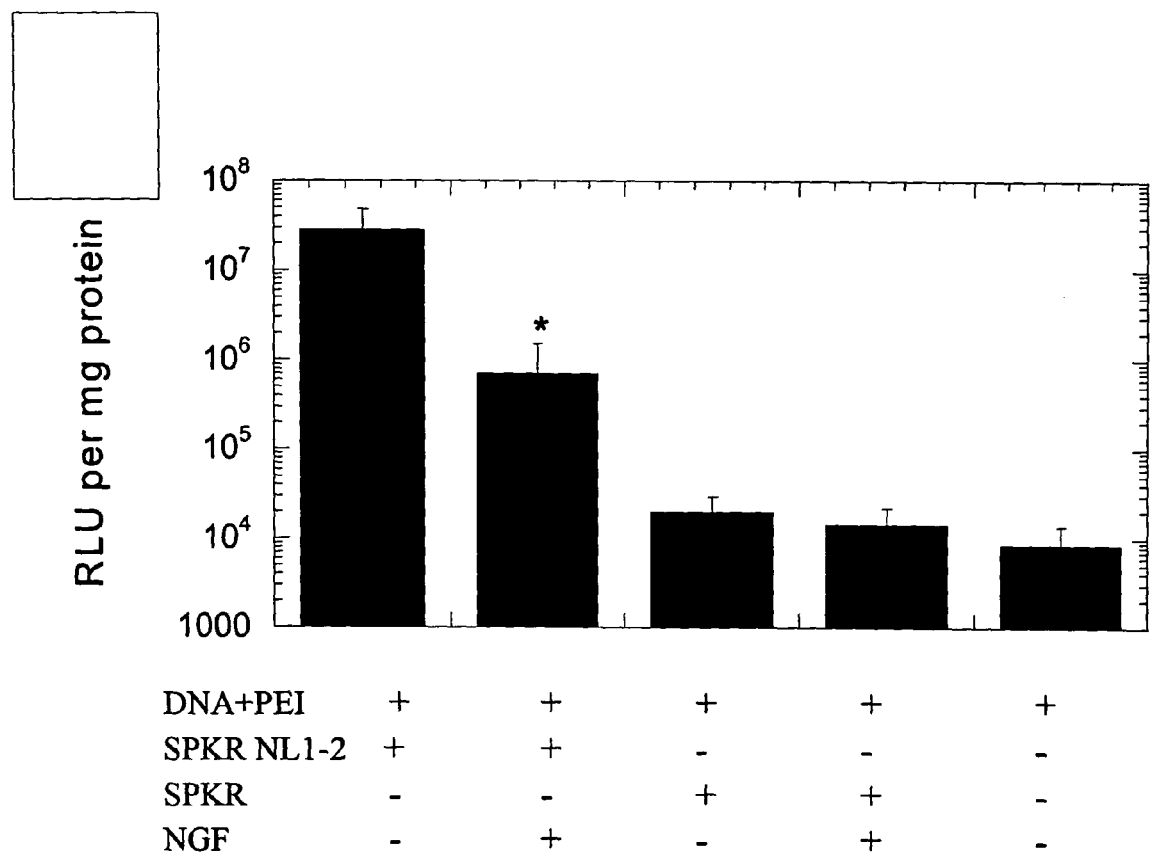

FIG. 7: Specificity of $SPKR_4NL1-2$-mediated gene expression. NGF inhibits gene expression mediated by $SPKR_4NL1-2$. PC12 cells were treated in a 48-well plate. To form complexes for each well, 0.5 μg of pCAGluc plasmid was first mixed with either $SPKR_4NL1-2$ or $(SPKR)_4$ at an N/P ratio of 2.5 and incubated for 30 min, after which PEI600 (N/P ratio of 10) was added and the mixture incubated for a further 30 min. NGF (200 ng/ml) was added to some wells during transfection. Luciferase activities were measured 24 h later and shown in relative light units (RLU)/mg protein. *P<0.05 compared to the cells treated with the same $SPKR_4NL1-2$/DNA/PEI600 complexes but without NGF.

Figure 8:
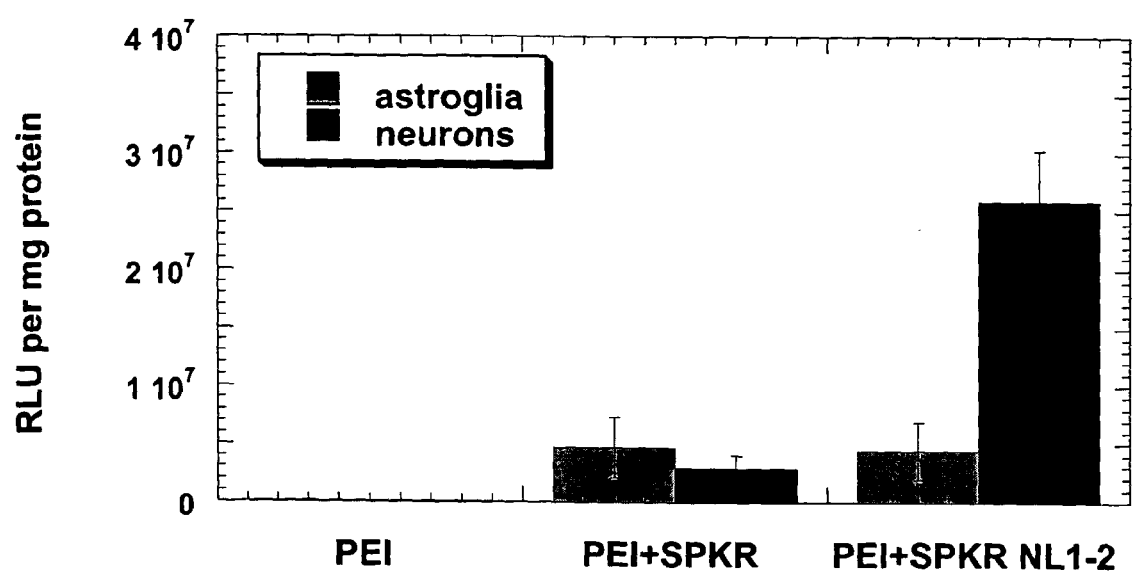

FIG. 8: Specificity of $SPKR_4NL1-2$-mediated gene expression. $SPKR_4NL1-2$ mediates gene delivery to neurons and glial cells. In a 48-well plate, primary rat cortical neurons or glial cells were transfected with $SPKR_4NL1-2$/DNA/PEI600, $(SPKR)_4$/DNA/PEI600, or DNA/PEI600 complexes. The complexes were prepared with 0.25 μg of DNA mixed with peptides, if present, and PEI600 at N/P ratios of 2.5 and 5, respectively. Luciferase activities were measured 24 h later and shown in relative light units (RLU)/mg protein. **P<0.01 compared to the neurons treated with DNA complexed with $(SPKR)_4$ and PEI600.

Figure 9:
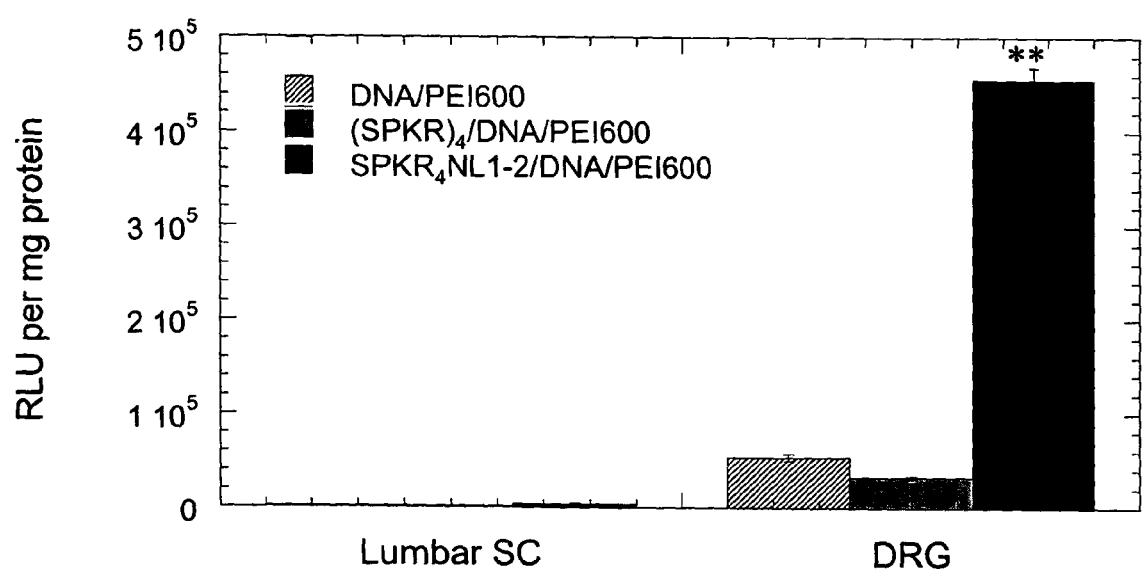

FIG. 9: $SPKR_4NL1-2$ mediates in vivo gene delivery to dorsal root ganglia (DRG). Complexes formed from 4 μg of pCAGluc, $SPKR_4NL1-2$ at an N/P ratio of 2.5, and PEI600 at an N/P ratio of 10 were injected intrathecally into the lumbar spinal cord in rats. DRG and the lumbar spinal cords were collected 3 days after injection. Results are expressed in relative light units (RLU)/mg protein. **P<0.01 compared to the rats treated with DNA complexed with $(SPKR)_4$/PEI600.

Figure 10:
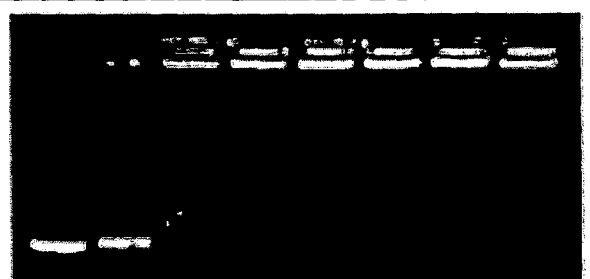
Figure 10:
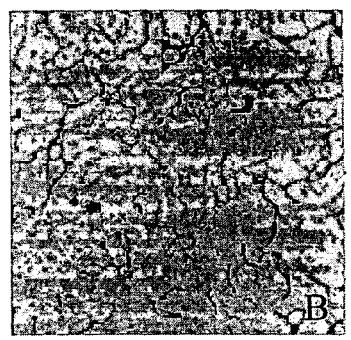
Figure 10:
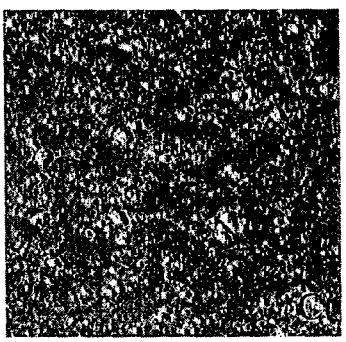
Figure 10:
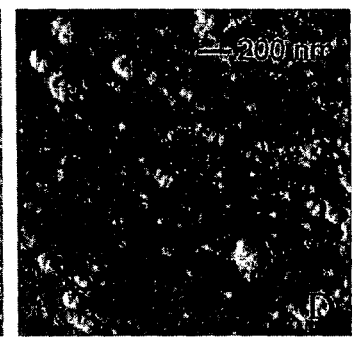

FIG. 10: SPKR$_4$BL1-2 binds and condenses DNA.
(A): SPKR$_4$BL1-2 binds to plasmid DNA and reduces its mobility during electrophoresis. The DNA is completely retarded at an N/P ratio of 2 (0.075 nmol of peptide with 0.1 μg of DNA).
(B)–(D): Atomic force microscopy images of DNA and SPKR$_4$BL1-2. Each image covers a field of 2 μm by 2 μm. (B) pCAGluc plasmid DNA. (C): SPKR$_4$BL1-2 peptide. (D) SPKR$_4$BL1-2 and plasmid DNA self-assemble into condensed particles.

Figure 11:
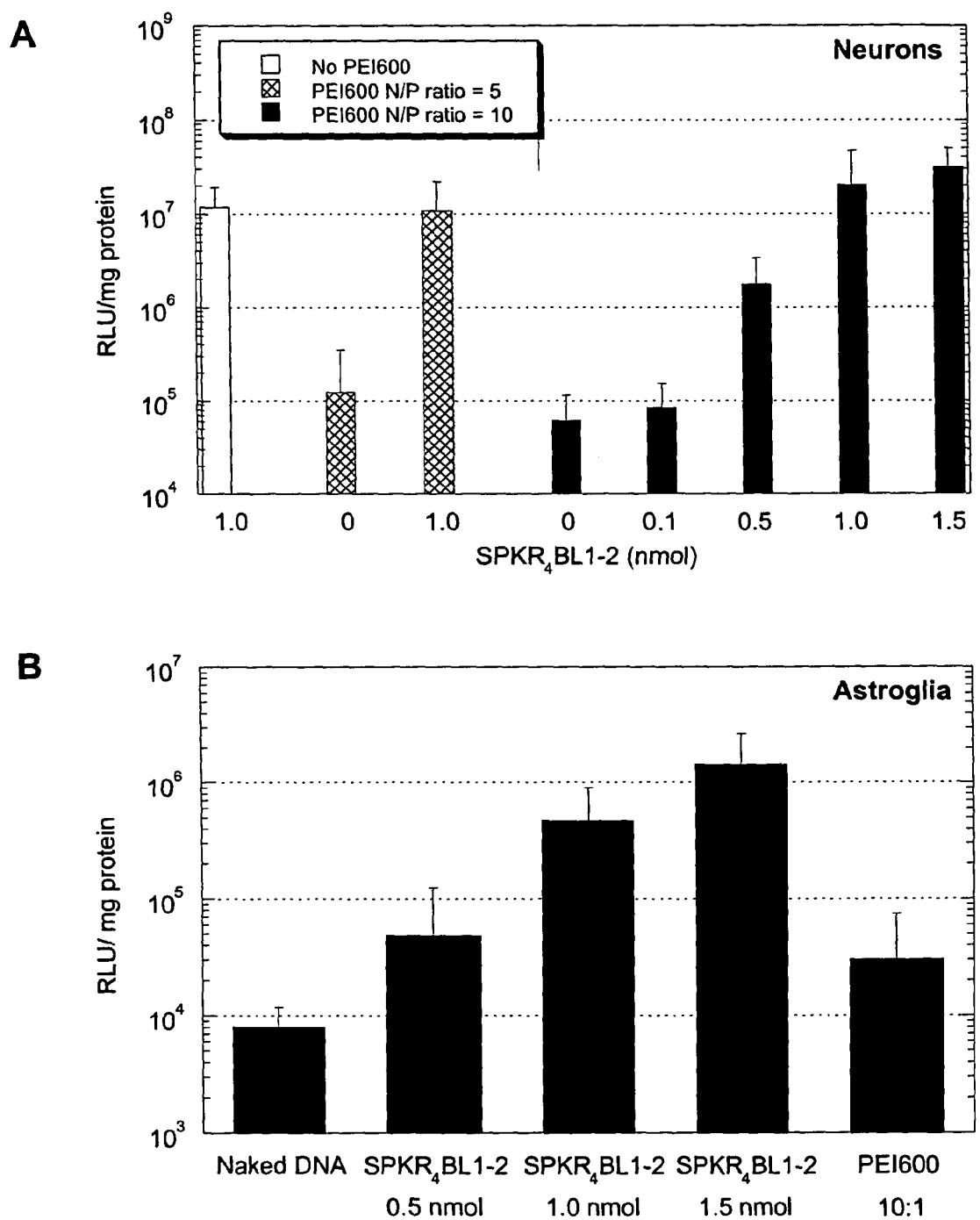

FIG. 11: SPKR$_4$BL1-2 mediates gene expression in rat primary cultures of neurons and astroglial cells.
(A): In a 48-well plate, cortical neurons were transfected with triple complexes of pCAGluc (0.25 μg/well), PEI600, and SPKR$_4$BL1-2. Luciferase activities were assayed 24 h later and are expressed as relative light units (RLU) normalized by total protein content, with error bars indicating one SD.
(B): In a 48-well plate, primary astroglial cells were transfected with pCAGluc/SPKR$_4$BL1-2 or pCAGluc/PEI600 complexes. 0.25 μg of pCAGluc was used per well. Transgene expression after 24 h is expressed as RLU/mg protein±SD.

Figure 12:
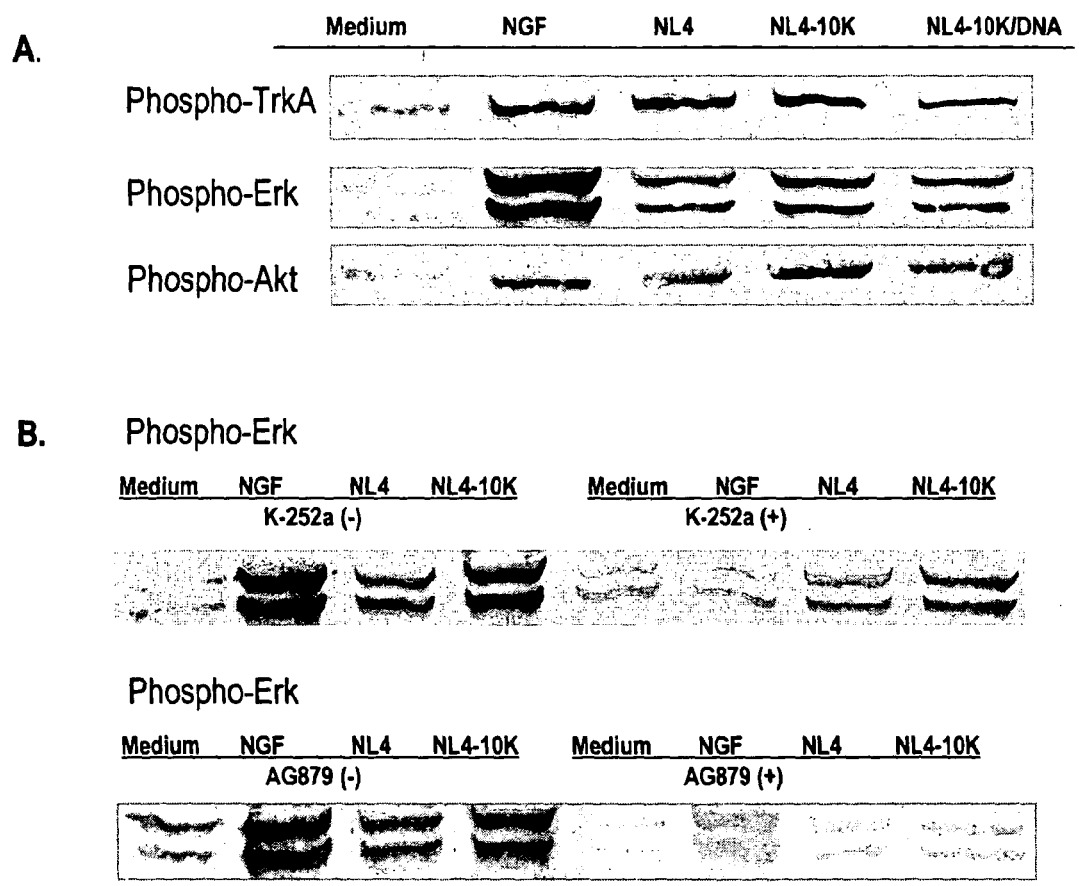

FIG. 12: NL4-10K activates TrkA, Erk and Akt.
(A): Activation of TrkA and its related signaling pathways. PC12 cell were incubated in RPMI-1640 medium containing 0.5% FBS and 0.25% horse serum and treated for 15 min with 10 ng/ml NGF, 5 μM NL4, 5 μM NL4-10K, NL4-10K/DNA complexes (N/P ratio of 5) or serum free RPMI-1640 without additives. The cell lysates were collected for Western blotting using primary antibodies against Phospho-TrkA, Phospho-p44/p42 MAPK or Phospho-Akt.
(B): TrkA inhibitors block NL4-10K-induced Erk activation. PC12 cells were preincubated with or without 100 nM K-252a or 10 μM AG879 for 10 min and then treated as described in (A). The cell lysates were collected for Western blotting using monoclonal antibodies against Phospho-p44/p42 MAPK.

Figure 13:
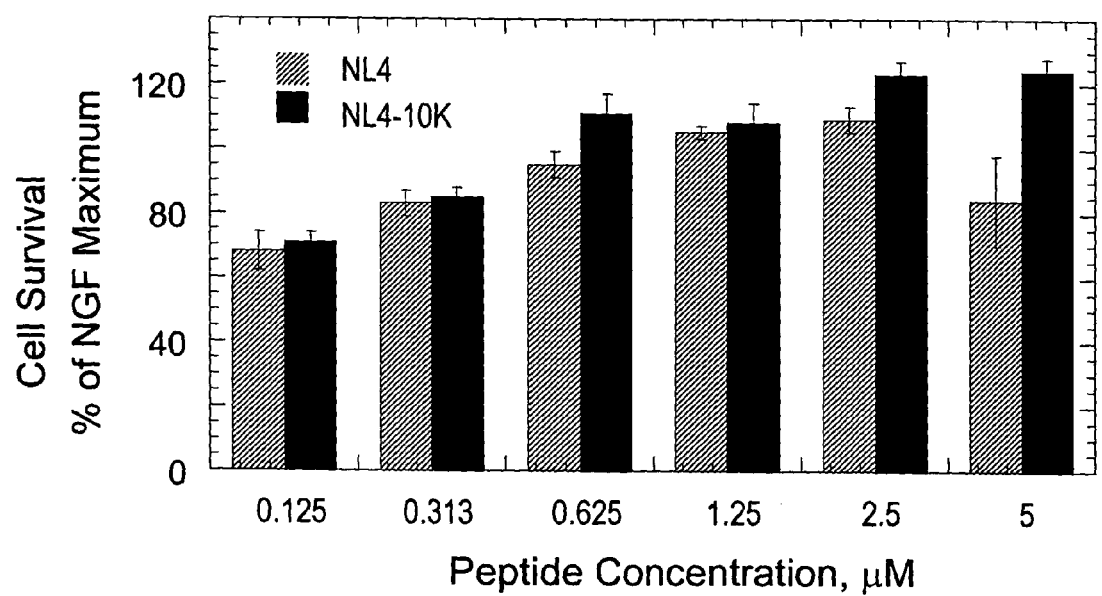

FIG. 13: NL4-10K promotes survival of neuronally differentiated PC12 cells in serum-free medium. Differentiated PC12 cells were deprived of serum and NGF for 4 days. NL4 and NL4-10K were added at the time of serum and NGF withdrawal and 10 ng/ml NGF was used as a positive control. Cell survival was estimated using a MTT assay. Cell survival mediated by the polypeptides was expressed as percentage of maximal NGF promoted survival.

Figure 14:
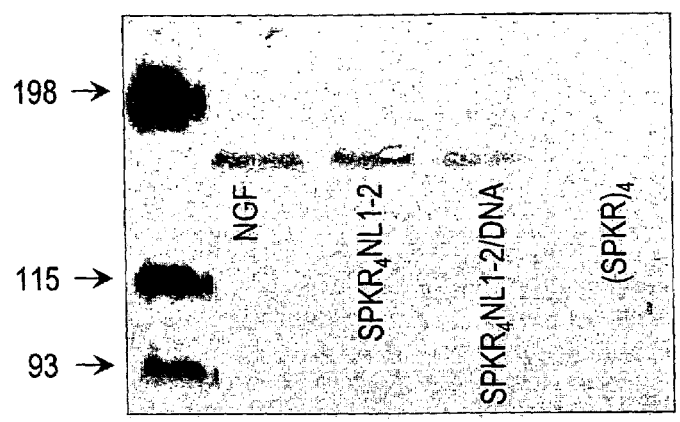
Figure 14:
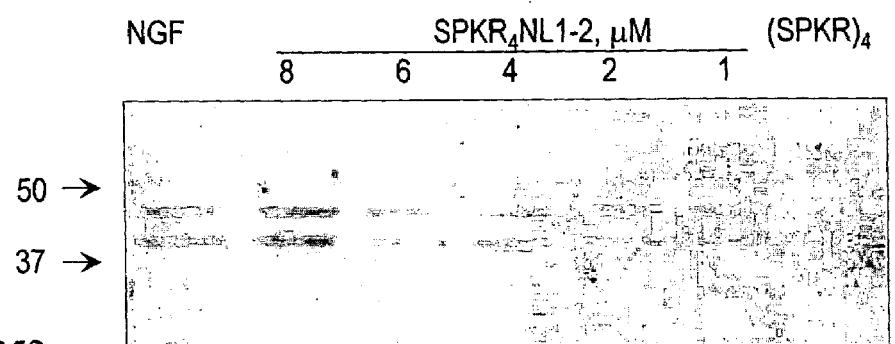
Figure 14:
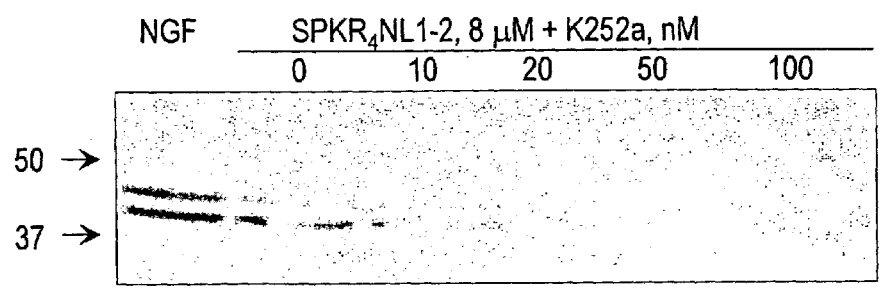

FIG. 14: SPKR$_4$NL1-2 activates TrkA and Erk. PC12 cells pre-incubated in RPMI-1640 medium containing 0.5% FBS and 0.25% horse serum for 2 days were treated for 20 min with NGF or peptides diluted in serum-free RPMI-1640. The cell lysates were analyzed by immunoblotting using primary antibodies specific to either phospho-TrkA or phosphorylated Erk 1 and 2.
(A): Phospho-TrkA Western blot. The cells were treated with NGF (20 ng/ml), SPKR$_4$NL1-2 (8 μM), SPKR$_4$NL1-2/DNA complexes (8 μM, N/P ratio of 5), or (SPKR)$_4$ (8 μM).
(B): Phospho-Erk Western blot. The cells were treated with NGF (20 ng/ml), various concentrations of SPKR$_4$NL1-2 from 1 to 8 μM, or 8 μM of (SPKR)$_4$.
(C): A TrkA inhibitor blocks SPKR$_4$NL1-2-induced Erk activation. The PC12 cells were pre-incubated with 0, 10, 20, 50 and 100 nM of K-252a (TrkA tyrosine kinase inhibitor) for 10 min before treatment with NGF (20 ng/ml) or SPKR$_4$NL1-2 (8 μM). Molecular weights of protein standards are shown on the left.

Figure 15:
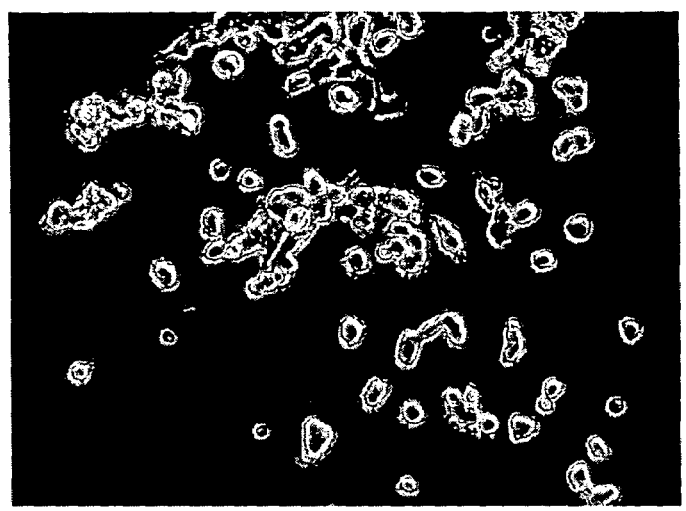
Figure 15:
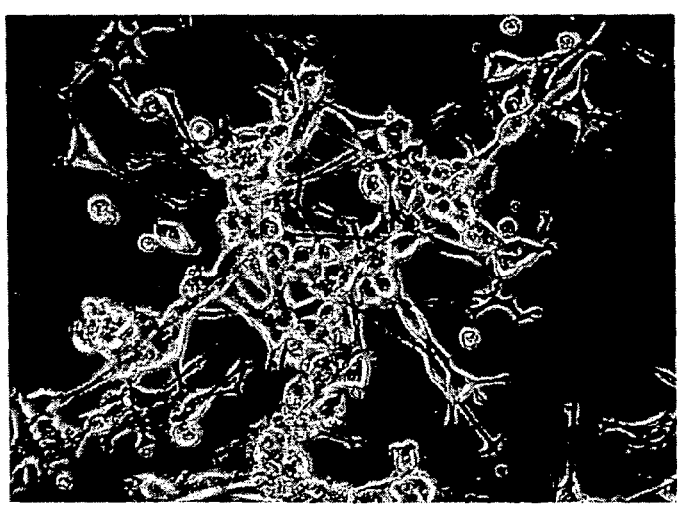
Figure 15:
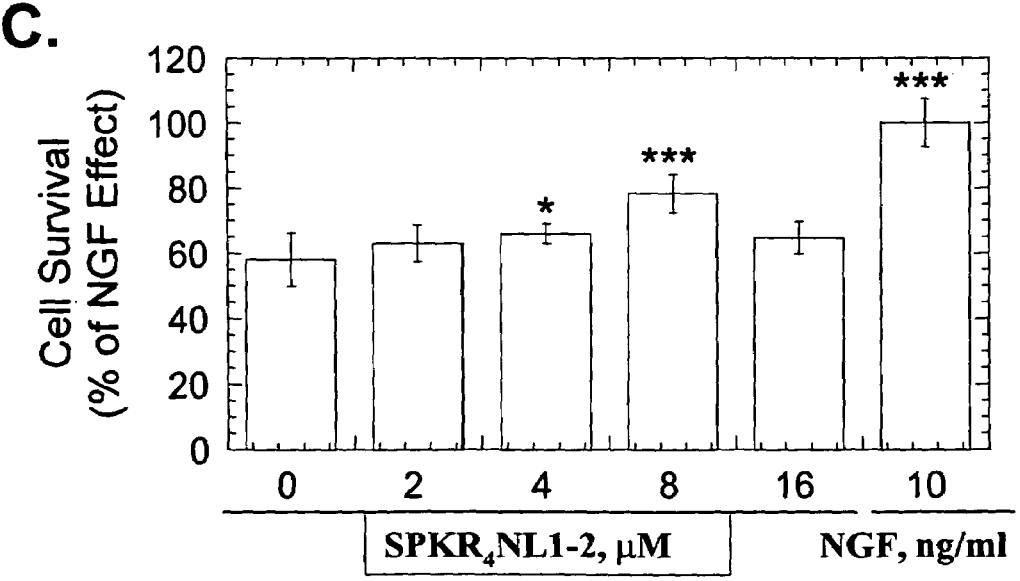

FIG. 15: SPKR$_4$NL1-2 has NGF-like bioactivity.
(A) & (B): SPKR$_4$NL1-2 promotes neurite outgrowth. PC12 cells were treated with 8 μM of (SPKR)$_4$ (A) or SPKR$_4$NL1-2 (B) for 3 days.
(C): SPKR$_4$NL1-2 promotes survival of PC12 cells deprived of serum for 3 days. Different concentrations of SPKR$_4$NL1-2, from 0 to 16 μM, were added at the time of serum withdrawal and 10 ng/ml of NGF was used as a positive control. Cell survival was estimated by an MTT assay and expressed as a percentage of maximal NGF-promoted cell survival.

DETAILED DESCRIPTION OF PREFERRED EMBODIMENTS

The term "polypeptide" is used herein synonymously with the term "protein" to refer to any polymer or chain of amino acids. Polypeptides may be linear, or cyclic. The terms "polypeptide" and "peptide" are distinguished only on the basis of the number of residues in the polymer. Generally speaking, the term "peptides" refers to amino acid polymers containing about 30 or fewer residues, more preferably 20 or fewer residues and most preferably about 10 or fewer residues. As used within, the term "amino acids" refers to the standard set of genetically encoded L-amino acids (alanine, cysteine, aspartic acid, glutamic acid, phenylalnaine, glycine, histidine, isoleucine, lysine, leucine, methionine, asparagine, proline, glutamine, arginine, serine, threonine, valine, tryptophan and tyrosine), and derivatives thereof. In the context of polypeptides or peptides created by semi-synthetic or chemical methods, the term "amino acid" also refers to all non-natural amino acids, as well as the D-isomers of the genetically encoded amino acids.

The present invention is derived, in part, from the applicant's surprising discovery that isolated hairpin motif fragments of a neurotrophin can selectively bind to neurotrophin receptors and retain the function of the full length neurotrophin. Such fragments, when combined with a nucleic acid binding element provide a means of selectively delivering nucleic acid to cells expressing neurotrophin receptors. The invention in one aspect therefore provides a recombinant polypeptide comprising a nucleic acid binding element and a cell targeting element which is a hairpin motif that selectively binds to a neurotrophin receptor. The invention, in another aspect provides a neurotrophin agonist comprising a hairpin motif that selectively binds to a neurotrophin receptor.

The term hairpin motif describes two adjacent hydrogen bonded β-strands connected by a loop region and as the term is used herein also describes two or more such structures in tandem. The length of the β-strands may vary but preferably is of sufficient length to form a stable β-sheet, meaning the β-strands remain hydrogen bonded, for example in physiological solutions. Therefore, the term, for example, describes a fragment of neurotrophin that forms a hairpin motif as defined herein but excludes a full length neurotrophin. The term "hairpin motif" also includes all functional equivalents as described below. The term "selectively binds to a neurotrophin receptor" or other similar terms are meant to describe binding to a neurotrophin receptor, while substantially not binding to other types of receptors. A cell targeting element does not substantially bind to a receptor if it does not affect the physiological functioning of the receptor.

The term neurotrophin in accordance with its usual definition in the art is used to describe a family of structurally and functionally related neurotrophic factors. Representative examples of neurotrophins include, but are not limited to nerve growth factor (NGF), brain derived neurotrophic factor (BDNF), neurotrophin-3 (NT3) and neurotrophin 4/5 (NT4/5). As used herein, the term neurotrophin generally refers to human neurotrophin, but also includes neurotrophins from any species including murine, bovine, ovine, porcine, equine and avian species. Reference to neurotrophin receptor includes p75$^{NTR}$ and neurotrophin tyrosine kinase receptors TrkA, TrkB and TrkC, and all other cognate receptors of a neurotrophin.

In different embodiments, the cell targeting element is a hairpin motif of a neurotrophin or a functional equivalent thereof. A hairpin motif of a neurotrophin is formed by a loop sequence and the β strand sequences immediately upstream and downstream to the loop sequence. The term "functional equivalent" is used to describe structurally and functionally related amino acids sequence that may differ from the parent amino acid by one or more deletions, substitutions, modifications or additions that do not affect selective binding to a neurotrophin receptor. For example, amino acids may be added to either end of the β strand without affecting the formation of the hairpin motif and selective binding to a neurotrophin receptor. In one embodiment, the functional equivalent will be substantially homologous, meaning that there is a substantial correspondence between the amino acid sequence of the equivalent and the parent amino acid sequence. In specific embodiments, the functional equivalent will be at least about 50%, 75%, 90% and 95% homologous.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology is established by recording all of the positions in which the amino acids of both sequences are identical, relative to the total number of positions.

In one embodiment, the functional equivalent differs from the hairpin motif sequence of a neurotrophin by one or more conservative amino acid substitutions. Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Generally, the functional equivalent will include one or more deletions, substitutions, modifications or additions in non-conserved sequences and generally amino acids important for binding a neurotrophin receptor will not be altered. The amino acid sequence of various neurotrophins, and their secondary structural elements have been studied and amino acids important for neurotrophin receptor binding have been identified, for example as described by Wiesmann et al. (Nature, 1999, 401: 184–188) for NGF. Homology among sequences from different species may be analyzed to determine conserved sequences using, as an example, the BLAST homology searching algorithm of Altschul et al., Nucleic Acids Res.; 25:3389–3402 (1997).

In specific embodiments, the polypeptide comprises aa 26–38, aa 41–49, aa 17–57, aa 69–79, or aa 81 to 107 of SEQ ID NO:1; aa 33–45, aa 48–56, aa 22–64, aa 76–86, or aa 88–115 of SEQ ID NO:2; aa 25–37, aa 40–48, aa 16–56, aa 68–78, or aa 80–107 of SEQ ID NO:3; aa 28–40, aa 43–52, aa 19–60, or aa 79–89, or aa 91–118 of ID NO:4, or a functional equivalent thereof.

In one embodiment, the polypeptide comprises amino acids 17–67 of human NGF:

SVSVWVGDKTTATDIKGKEVMVLG (aa 17–67 of SEQ ID NO:1)

EVNINNSVFKQYFFETKCRDPNPV

DSG

In this embodiment the cell targeting element consists of a hairpin motif of NGF formed by aa 17–57 and additional 10 amino acids that do not affect the formation of the hairpin motif or selective binding to a neurotrophin receptor. The additional 10 amino acids have been included to facilitate expression of the recombinant polypeptide.

In one embodiment, the polypeptide comprises amino acids 80–108 of human NGF:

CTTTHTFVKALTMDGKQAAWRFIR (aa 80–108 of SEQ ID NO:1)

IDTAC

In this embodiment, the cell targeting element consists of a hairpin motif of NGF formed by aa 81–107 and a cysteine at either end.

In one embodiment, the polypeptide comprises amino acids 22–74 of human BDNF and has the following sequence:

SISEWVTAADKKTAVDMSGGTCTV (aa 22–74 of SEQ ID NO:2)

LEKVOVSKGQLKQYFYETKCNPMG

YTKEG

In this embodiment, the cell targeting element consists of a hairpin motif formed by aa 22–64 of BDNF and additional 10 amino acids that enhance stable expression of the polypeptide.

Other suitable cell targeting elements may be identified by methods known to a person skilled in the art, for example, by testing for selective binding to a neurotrophin receptor. Neurotrophin receptor binding may be assayed, for example, by displacement/competitive binding assays using cells expressing the cognate receptors (See generally Ilag et al J.Biol.Chem. 269:19941–19946 and references therein; Ruden et al J. Biol. Chem 217:5623–5627). As used herein, the term "cognate receptor" refers to a cell surface receptor capable of selectively binding a specific neurotrophin. For example, TrkA is a cognate receptor for NGF, TrkB is a cognate receptor for BDNF. The p75$^{NTR}$ receptor is a low affinity cognate receptor for NGF, BDNF, NT-3 and NT4/5. In the displacement/competition assays, the ability of a cell targeting element to bind to a neurotrophin receptor is demonstrated by the reduced binding of a labelled full-length neurotrophin to its cognate receptor. The methods for performing the competition/displacement assays would be known to a person skilled in the art. For example, the Rat pheochromocytoma cell line PC12 expresses TrkA and $p75^{NTR}$ receptors and may be used in a competition assay with labeled NGF and polypeptide comprising a putative receptor-binding element.

Alternatively, where the cell targeting element is a neurotrophin agonist, the binding assays may be designed around the endogenous tyrosine kinase activity of Trk receptors. When the cell expressing Trk receptors are incubated with a cell targeting element and in the presence of a source of $^{32}P$ phosphate, ligand binding can be measured by the amount of radiolabeled phospho-Trk receptors. Alternatively, the neurotrophin agonist binding may be determined by any one of a number of downstream kinase substrates in the Trk signaling pathway, for example Erk1, Erk2 or Akt. A person skilled in the art would know how to detect the radiolabled phosphoproteins, for example through immunoblotting techniques.

Alternatively, putative cell targeting elements that act as neurotrophin agonists may be screened for their ability to promote nerve cell survival. For example seeded PC12 cells exposed to serum-free media have reduced viability, but the survival rate can be increased by including NGF in the culture media. Putative agonistic cell targeting element may be screened for their ability to promote cell survival in serum-free media.

Neurotrophins have six cysteine residues that are oxidized to form a cystiene knot motif. Other growth factors, including platelet derived growth factor (PDGF) (Oefner et al EMBO J 11: 3921-26, 1994), transforming growth factor-B (TGF-B) (Schlunegger et al Nature 358:430–434, 1992) and chorionic gonadotropin (Lapthorn et al Nature 369: 455–61, 1994) also have cysteine knot motifs. Human NGF has three disulfide bonds, between cysteines 15–80, 58–108 and 68–110. Heterologous expression of BDNF in *E. Coli* results in 10 forms with improper disulfide pairing, resulting in reduced biological activity (Shimizu et al, Biosci. Bitech. Bichem. 60; 971–974, 1996). As the recombinant polypeptide of the invention only includes a portion of a neurotrophin sequence, residues not implicated in receptor binding may be deleted, including any cysteine residues, thereby avoiding the problems associated with disulfide scrambling in the full length neurotrophin. Furthermore, a smaller neurotrophin binding element may be less immunogenic than a full length neurotrophin.

If the hairpin motif contains cysteine residues, the sequence may be modified by conventional techniques to delete or substitute cysteine so that only two cysteine residues are present in the hairpin motif. One or more cysteine residues in the hairpin motif may also be moved, or cysteine residues added so that a cysteine residue is present at the amino and carboxy termini of the hairpin motif to form a intramolecular disulfide bond. In various embodiments, the thiol groups of the two cysteine residues can be oxidized to form an intramolecular disulfide bond. Formation of a disulfide may be accomplished by conventional means known to a person skilled the art of protein chemistry, for instance by air oxidation. Without being limited to any particular theory, it is believed that formation of an intramolecular disulfide will stabilize the hairpin motif, and may increase the affinity of the motif for a cognate receptor. The problem of mismatched disulfide bonds or disulfide scrambling can be avoided by including only two cysteine residues in a sequence. In one embodiment, the disulfide bond is at the open end of the β-hairpin motif.

The nucleic acid binding element may be any amino acid sequence that binds nucleic acid in either a sequence-specific or a sequence-independent manner. In one embodiment, the nucleic acid binding element is a DNA binding element. DNA binding elements are known in the art, and include, for example, the DNA binding domains from transcription factors. Generally speaking, transcriptions factors generally bind DNA in a sequence specific manner. What is meant by "sequence-specific" is that the receptor selectively recognizes a specific DNA sequence, or alternatively a small number of highly related sequences. In some embodiments the DNA binding element may be derived from the transcription factors whose DNA binding domains contain any one of the following structural motifs: helix-turn-helix proteins (λCro, λcI, *E.coli* CAP proteins. Lac repressor, Trp repressor (Steisz et al PNAS 79:3097–3100, 1982; Ohlendorf et al J. Mol Bio 169:757–769, 1983; Kaptein et al J.Mol Biol. 182:179–182, 1985; Sheritz et al Nature 317:782–786;) homeodomains (Antennapaedia and MATα2 (Qian et all, Cell 59:573–580; Wolberger et al Cell 59: 573–580)), zinc finger proteins (TFIIA, Sp-1, Zif268, see generally Krizek et al JACS 113: 4518–4523:1991), steroid receptors, leucine zippers proteins (C/EBP, c-fos, c-jun, GCN4, CREB (see generally O'Shea et al Science 24:539–544), helix-loop-helix proteins (MyoD and c-myc (Weinrib et al Science 251:761–766, 1991) and B-sheets (Met J, Arc and Mnt represors (Phillips, Current Opinion in Struc Biol 1: 89–98, 1991; Berg et al Nature 346:586–589, 1990)). Alternatively other DNA binding elements include the DNA binding domains of GAL4 repressor, and the RRE (rev responsive element) from HIV.

Many transcription factors are cloned, and their sequences are available on public databases. Alternatively, the sequence-specific DNA-binding domains may be derived from proteins that are not transcriptions factors, for instance restriction endonucleases and the like. In various embodiments the invention contemplates the use of full-length DNA binding domains, as well as fragments of any DNA binding domain that retain the ability to bind DNA.

In various other embodiments, the DNA-binding element binds DNA in a sequence-independent manner. By "sequence-independent", it is meant that the protein binds DNA with little specificity for a specific DNA sequence. Suitable sequence-independent binding elements may be derived from the amino acid sequences of the DNA-binding domains of highly basic proteins such as histones or protamines. In a specific embodiment, the DNA binding element is DNA binding-domain of Histone H1 first used by Fortunati et al (Gene Therapy 2000; 7: 1505–15) and has the following sequence:

SPKRSPKRSPKRSPKR (SEQ ID NO:11)

In one embodiment, the DNA binding element may be a positively charged domain, for example, a cationic polypeptide such as poly-lysine, poly-arginine, or any other polymer of amino acids having basic side chains. Cationic polymers are believed to bind DNA in a sequence-independent manner through electrostatic interactions between the cationic polymer and the anionic nucleic acid phosphate backbone. It would be understood by a person skilled in the art that the strength of the interaction between a cationic polymer and DNA will reflect, among other things, the number of cationic monomers in the polymer, and more particularly the overall net charge of the cationic polymer. In a specific embodiment of the present invention, the DNA-binding element is deca-lysine (i.e. KKKKKKKKKK, SEQ ID NO:10). As discussed below, such positively charged domain may also bind to cell surface, and thereby enhance the binding of the hairpin motif to a neurotrophin receptor.

A person skilled in the art can readily identify other suitable DNA-binding elements. For example, sequence specific DNA binding may be assayed by conventional gel retardation assays employing nucleic acids containing one or more DNA recognition sequences. Alternatively, where the DNA binding element is cationic and binds in a sequence independent manner, DNA binding may be assayed by measuring the electrophoretic mobility of the target DNA in the presence and absence of the putative DNA binding element. DNA binding by a cationic polymer will decrease the net charge on the DNA-binding element complex, and will retard electrophoretic migration of the complex relative to the unbound DNA. The electrophoretic mobility of the complexes may be determined by conventional agarose gel electrophoresis, and the DNA visualized by ethidium bromide staining.

In one embodiment, the DNA binding element and the cell targeting element may be contiguous, for example, the carboxy terminal residue of the nucleic acid binding element may be covalently linked to the amino terminal residue of the cell targeting element.

In different embodiments, the polypeptide may further comprise a linker sequence between the DNA binding element and the cell targeting element to enhance the DNA binding and/or neurotrophin receptor binding by providing sufficient conformational flexibility to allow joined elements to function essentially independently to each other.

In one embodiment, the linker sequence is a sequence of genetically encoded amino acids. Preferably the linker sequence does not include a cysteine.

Suitable linker/spacer elements would be known to a person skilled in the art, and include polypeptide sequences of less than about 20 amino acids that contain a high percentage of small uncharged amino acids (i.e. glycine, serine, threonine, tyrosine, asparagine and gluatamine). Of these amino acids, linkers with a high percentage of serine and glycine residues are particularly preferred.

Alternatively, a suitable linker/spacer element may contain a sequence known to adopt a specific secondary structure. In some embodiments, the linker sequence forms an α-helical structure. An α-helical linker sequence may prevent successive functional elements from interacting and/or aggregating. In a specific embodiment, the linker sequence is an H1 α-helix and has the following amino acid sequence: TYLSEDELKAAEAAFKRHNPT (SEQ ID NO:30)

In another embodiment, the polypeptide further comprises a disulfide bond isomerase. Without being limited to any specific theory, it is believed that disulfide bond isomerase activity will enhance the solubility, stability and folding of the polypeptide. For instance, the disulfide bond isomerase may prevent polypeptide aggregation by reducing any intermolecular disulfide bonds. The disulfide bond isomerase may also promote disulfide exchange in favour of the most stable disulfide bond. In various embodiments, the polypeptide may comprise other elements that catalyze protein folding, stability and solubility, including, but not limited to, proline peptide isomerase.

In another embodiment, the polypeptide comprises a marker or tag such as a histidine tag that facilitate the preparation, isolation or purification of the polypeptide. Histidine tags are sequences of poly-histidine that have been shown to have affinity for divalent metal ions, such as copper, or more preferably nickel or cobalt. It is known to the person skilled in the art that such histidine tags may be exploited in immobilized metal affinity chromatography (IMAC) protein purification step. Generally, the his-tagged protein is incubated in solution with an immobilized metal ion. His-tagged proteins will associate with the immobilized metal, whereas proteins that do not contain a His-tag are washed away. After a washing step, the his-tagged proteins are eluted off the immobilized metal support by the addition of a metal chelator such as EDTA or a by a high concentration of imidazole. The length of the histidine-tag is preferably 6 residues long ($His_6$) and more preferably 8 or 10 residues long. ($His_8$ or $His_{10}$). In a specific embodiment, the polypeptide comprises a histidine-tag of ten residues ($His_{10}$). Histidine tags may also facilitate gene delivery since the imidazole heterocycle structure in histidine displays a $pK_a$ around 6 thus possessing a buffering capacity in the endolysosomal pH range. This property may facilitate vesicular escape of DNA through a "proton sponge" mechanism.

The polypeptide may comprise one or more cell targeting elements, operably positioned such that each cell targeting element may bind to a neurotrophin receptor. Similarly, the polypeptide may contain multiple DNA-binding elements. For example, a polypeptide comprising more than one cell targeting element may be particularly preferred where the full length ligand normally binds to a receptor dimer as it may bind more strongly and/or more specifically to such a receptor, (eg Trk family homodimers or $p75^{NTR}$—Trk heterodimers). This increased binding is expected to increase efficiency of the internalization of the fusion proteins by receptor mediated endocytosis.

In one embodiment, the polypeptide comprises the following sequence:
CTTTHTFVKA LTMDGKQAAW RFIRIDTACK KKKKKKKKK (SEQ ID NO:5)

This 29 amino acid sequence was generated by combining amino acids 80–108 of human NGF and a 10-lysine sequence that can bind to and condense DNA into a compact structure. The hairpin motif consists of four amino acid residues of loop L4 of NGF and parts of C and D β-strands of NGF to stabilize the natural conformation of the loop through the formation of hydrogen bonds between two β-strands. The three-dimensional structure is further stabilized by the disulfide bond formed between C80 and C108 after oxidation.

In another embodiment, the DsbC protein, an *E-coli* disulfide bond isomerase was added to the amino terminus of the hairpin motif and the polypeptide in this embodiment comprises the following sequence:

```
MKKGFMLFTL LAAFSGFAQA DDAAIQQTLA KMGIKSSDIQ PAPVAGMKTV (SEQ ID NO:6)

LTNSGVLYIT DDGKHIIQGP MYDVSGTAPV NVTNKMLLKQ LNALEKEMIV

YKAPQEKHVI TVFTDITCGY CHKLHEQMAD YNALGITVRY LAFPRQGLDS

DAEKEMKAIW CAKDKNKAFD DVMAGKSVAP ASCDVDIADH YALGVQLGVS

GTPAVVLSNG TLVPGYQPPK EMKEFLDEHQ KMTSGKGSTS GSGHHHHHHS

AGLVPRGSCT TTHTFVKALT MDGKQAAWRF IRIDTACKKK KKKKKKK
```

In another embodiment, the polypeptide comprises the following sequence:

MGHHHHHHHH HHSSGHIEGR HMSPKRSPKR SPKRSPKRGG TYLSEDELKA (SEQ ID NO:7)
AEAAFKRHNP TGSCSVSVWV GDKTTATDIK GKEVMVLGEV NINNSVFKQY
FFETKCRDPN PVDSG

In this embodiment, the hairpin motif is generated by loops L1 and L2 of NGF, together with A and B β strands derived from residues 17–67 of human NGF. (SPKR)$_4$, from Histone H1, which can condense DNA upon binding to the minor groove, is used as a non-specific, nucleic acid binding moiety (Khadake J R and Rao M R, Biochemistry 36: 1041–1051, 1997). These two elements are separated by an α-helical linker sequence flanked by flexible glycine sequences to enhance independent action of the cell targeting element and the nucleic acid-binding element, in particular, the flexible interaction of the loop structures with neurotrophin receptors. The $His_{10}$ tag is used for peptide purification and may play a role in the escape of endocytosed polypeptide/DNA complexes. To stabilize polypeptide conformation, a cysteine residue was added immediately before aa 17–67 of human NGF in order to facilitate the formation of a disulfide bond with cysteine 58 of NGF.

In another embodiment, the polypeptide comprises the hairpin motifs of loops L1 and L2 of BDNF (aa 22–74), $(SPKR)_4$ and an alpha-helix linker and comprises the following amino acid sequence:

```
MGHHHHHHHH HHSSGHIEGR HMSPKRSPKR SPKRSPKRGG TYLSEDELKA (SEQ ID NO:8)
AEAAFKRHNP TGSCSISEWV TAADKKTAVD MSGGTVLE   KVPVSKGQLK
QUFYETKCNP MGYTKEG
```

The polypeptides of this invention can be prepared by methods known in the art, including by conventional chemical means, for example, solid state synthesis employing t-Boc or Fmoc amino acid derivatives. Alternatively, polypeptides may be expressed using recombinant DNA technology and an appropriate expression system. Particularly advantageous are cellular expression systems wherein the gene encoding for a polypeptide of the invention is transcribed and translated. Examples of suitable expression systems included but are not limited to expression in *E. Coli, S. cerevisiae, Pichia pastoris*, baculovoirus/insect cells expression systems and eukayotic cells in culture. Expression in any of these systems may be driven by constitutive or inducible promoters.

The expressed polypeptide can be purified and isolated from other biological or chemical constituents by conventional techniques, including chromatography, immunoprecipitation and the like. The purity of the purified proteins may be assessed by electrophoretic or chromatographic techniques. The identity of the purified polypeptide may also be confirmed by mass spectrometry techniques and, where required, by MS/MS sequencing.

In various aspects, the present invention provides a recombinant nucleic acid molecule from which a polypeptide of the invention may be expressed. The invention therefore provides a recombinant nucleic acid molecule encoding a polypeptide of the invention. The nucleic acid may be RNA, or DNA. The DNA may be single stranded or more preferably double stranded, and most preferably circular doubled stranded. DNA encoding the polypeptides of the invention may be determined from the known sequence of the polypeptides using methods known in the art. The DNA sequences for neurotrophins are known and available in public databases such as genbank. With the knowledge of the neurotrophin sequence, a person skilled in the art can readily design oligonucleotide primers such that DNA molecules encoding fragments of nueurotrophin sequences could be amplified from neurotrophin cDNA or mRNA by polymerase chain reaction. Similarly, the nucleotide sequences of a linker sequence, histinde tags and nucleic binding elements may be derived using an appropriate genetic code. Preferably, nucleic acid sequences comprising codons with a high codon bias are used to prevent misincorporation and high levels of protein expresion in any particular expression host (see generally Calderone et al. J Mol Biol 1996, 262(4):407–412. In various embodiments, the nucleic acid molecule comprises the sequence of SEQ ID NO: 14, SEQ ID NO: 26, SEQ ID NO: 29 and SEQ ID NO: 31.

The recombinant nucleic acid molecule of the present invention may be constructed by standard techniques known to someone skiled in the art and described, for example in Sambrook et al. in Molecular Cloning: A Laboratory Manual, $3^{rd}$ Edition, Cold Spring Harbour, Laboratory Press and other laboratory manuals. Nucleic acid molecules may be chemically synthesized using techniques such as disclosed, for example, in Itakura et al U.S. Pat. No. 4,598,049; Caruthers et al U.S. Pat. No. 4,458,066; and Itakura et al U.S. Pat. Nos. 4,401,796 and 4,373,071.

Nucleic acids molecules may also be isolated and combined. By isolated it is meant that the isolated subtance has been substantially separated or purified away from other components, such as biological components, with which it would otherwise be associated, for example in vivo, so that the isolated substance may itself be manipulated or processed. The term isolated therefore includes substances purified by standard purification methods, as well as substance purified by recombininat expresion in a host, as well as chemically synthesized substances. A variety of strategies are available for combing and ligating individual nucleic acid molecules, and depending on the nature or the termini of the the nucleic acids to be ligated, a suitable strategy will readily be apparent to one skiled in the art. As will be apparent to a person skilled in the art of molecular biology, the DNA fragments must be ligated in the proper frame to ensure that the resulting gene encodes for the desired amino acid sequence.

Another aspect of the invention provides an expression vector comprising the recombinant nucleic acid molecule of the invention. The vector may be a plasmid or a virus or virus derived. The construction of such a vector by standard techniques will also be well known to one of ordinary skill in the art. The vectors of the present invention may also contain other sequence elements to facilitate vector propagation and selection in host cells for example, coding sequences for selectable markers, and reporter genes, known to persons skilled in the art. In addition, the vectors of the present invention may comprise a sequence of nucleotides for one or more restriction endonuclease recognition sites.

An expression vector of the present invention may be introduced into a host cell, which may include a cell capable of expressing the protein encoded by the expression vector. Accordingly, the invention also provides host cells containing an expression vector of the invention. The term "host cell" refers not only to the particular subject cell but to the progeny or potential progeny of such a cell. Because certain modifications may occur in succeeding generations due to either cellular differentiation, mutation or environmental influences, such progeny may not, in fact, be identical to the parent cell, but are still included within the scope of the term as used herein.

Vector DNA can be introduced into cells by conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells are well known in the art and can for example be found in Sambrook et al. (Molecular Cloning: A Laboratory Manual, 3rd Edition, Cold Spring Harbor Laboratory press (2001)), and other laboratory manuals.

A cell, tissue, organ, or organism into which has been introduced a foreign nucleic acid, is considered "transformed", "transfected", or "transgenic". A transgenic or transformed cell or organism also includes progeny of the cell or organism and progeny produced from a breeding program employing a transgenic organism as a parent and exhibiting an altered phenotype resulting from the presence of a recombinant nucleic acid construct. A transgenic organism is therefore an organism that has been transformed with a heterologous nucleic acid, or the progeny of such an organism that includes the transgene. The invention in various aspects provides a transgenic cell and a non-human animal comprising a recombinant nucleic acid molecule according to various embodiments of the invention.

For stable transfection of mammalian cells, it is known that, depending upon the expression vector and transfection technique used, only a small fraction of cells may integrate the foreign DNA into their genome. In order to identify and select these integrants, a gene that encodes a selectable marker (such as resistance to antibiotics) may be introduced into the host cells along with the gene of interest. Preferred selectable markers include those that confer resistance to drugs, such as G418, hygromycin and methotrexate. Nucleic acids encoding a selectable marker may be introduced into a host cell on the same vector as that encoding the peptide compound or may be introduced on a separate vector. Cells stably transfected with the introduced nucleic acid may be identified by drug selection.

In one embodiment, the DNA expression vector comprises the following sequence:

```
ATGAAGAAAG GTTTTATGTT GTTTACTTTG TTAGCGGCGT TTTCAGGCTT    50 (SEQ ID NO:14)

TGCTCAGGCT GATGACGCGG CAATTCAACA AACGTTAGCC AAAATGGGCA   100

TCAAAAGCAG CGATATTCAG CCCGCGCCTG TAGCTGGCAT GAAGACAGTT   150

CTGACTAACA GCGGCGTGTT GTACATCACC GATGATGGTA AACATATCAT   200

TCAGGGGCCA ATGTATGACG TTAGTGGCAC GGCTCCGGTC AATGTCACCA   250

ATAAGATGCT GTTAAAGCAG TTGAATGCGC TTGAAAAAGA GATGATCGTT   300

TATAAAGCGC CGCAGGAAAA ACACGTCATC ACCGTGTTTA CTGATATTAC   350

CTGTGGTTAC TGCCACAAAC TGCATGAGCA AATGGCAGAC TACAACGCGC   400

TGGGGATCAC CGTGCGTTAT CTTGCTTTCC CGCGCCAGGG GCTGGACAGC   450

GATGCAGAGA AAGAAATGAA AGCTATCTGG TGTGCGAAAG ATAAAAACAA   500

AGCGTTTGAT GATGTGATGG CAGGTAAAAG CGTCGCACCA GCCAGTTGCG   550

ACGTGGATAT TGCCGACCAT TACGCACTTG GCGTCCAGCT TGGCGTTAGC   600

GGTACTCCGG CAGTTGTGCT GAGCAATGGC ACACTTGTTC CGGGTTACCA   650

GCCGCCGAAA GAGATGAAAG AATTTCTCGA CGAACACCAA AAAATGACCA   700

GCGGTAAAGG ATCAACTAGT GGTTCTGGTC ATCACCATCA CCATCACTCC   750

GCGGGTCTGG TGCCACGCGG TAGTTGTACC ACGACTCACA CCTTTGTCAA   800

GGCGCTGACC ATGGATGGCA AGCAGGCTGC CTGGCGGTTT ATCCGGATAG   850

ATACGGCCTG TAAAAAAAAA AAAAAAAAA AAAAAAAAA ATGA
```

In another embodiment, the DNA expression vector comprises the following sequence:

```
ATGGGCCATC ATCATCATCA TCATCATCAT CATCACAGCA GCGGCCATAT  50 (SEQ ID NO:26)
CGAAGGTCGT CATATGAGTC CGAAACGCAG CCCGAAACGT AGCCCAAAGC 100
GTAGCCCGAA GCGTGGCGGT ACCTACCTGT CTGAAGATGA GCTGAAAGCG 150
GCGGAGGCGG CATTCAAACG TCACAACCCG ACTGGATCCT GCAGTGTCAG 200
CGTGTGGGTT GGGGATAAGA CCACCGCCAC AGACATCAAG GGCAAGGAGG 250
TGATGGTGTT GGGAGAGGTG AACATTAACA ACAGTGTATT CAAACAGTAC 300
TTTTTTGAGA CCAAGTGCCG GGACCCAAAT CCCGTTGACA GCGGGTGA
```

In yet another embodiment, the DNA expression vector comprises the following sequence:

```
ATGGGCCATC ATCATCATCA TCATCATCAT CATCACAGCA GCGGCCATAT  50 (SEQ ID NO:29)
CGAAGGTCGT CATATGAGTC CGAAACGCAG CCCGAAACGT AGCCCAAAGC 100
GTAGCCCGAA GCGTGGCGGT ACCTACCTGT CTGAAGATGA GCTGAAAGCG 150
GCGGAGGCGG CATTCAAACG TCACAACCCG ACTGGATCCT GCAGTATTAG 200
TGAGTGGGTA ACGGCGGCAG ACAAAAAGAC TGCAGTGGAC ATGTCGGGCG 250
GGACGGTCAC AGTCCTTGAA AAGGTCCCTG TATCAAAAGG CCAACTGAAG 300
CAATACTTCT ACGAGACCAA GTGCAATCCC ATGGGTTACA CAAAAGAAGG 350
CTGA
```

The polypeptides of the invention can be used to effect neurotrophin receptor mediated delivery of nucleic acid, such as DNA bound to the nucleic acid binding element of the polypeptide. The nucleic acid may also be RNA, including sense RNA, anti-sense RNA, or a ribozyme. In one aspect therefore, the invention provides a composition comprising a polypeptide according to the invention and a nucleic acid. The polypeptide and the nucleic acid may form a non-covalent complex. The term "non-covalent" refers to all atomic or molecular interactions other than covalent bonds (ie where electrons are shared between two atoms). As used herein "non-covalent" includes, but is not limited by, the following interactions: electrostatic or ionic bonds, hydrogen bonds, dipolar interactions, hydrophobic interactions, van der Walls contacts, and aromatic stacking interactions. Generally speaking, non-covalent bonds are much less stable than covalent bonds and can usually be reversible formed and broken. In different embodiments, the non-covalent complex may be formed as a result of the electrostatic interactions between the negatively charged phosphate backbone of nucleic acids and the positively charged side chains of a non-specific DNA binding element.

In one embodiment, the nucleic acid comprises a coding gene sequence. In one embodiment of the present invention, the coding sequence is a therapeutic gene sequence. Therapeutic gene sequences include, but are not limited to, genes coding for proteins, sense RNA, anti-sense RNA or ribozymes, including molecules with neurotrophic, anti-apoptotic or anti-oxidant activities. Alternatively, therapeutic gene sequence may be used to effect genetic therapy by replacing or supplementing a endogenous defective gene, or by encoding an endogenous or exogenous gene product.

In another embodiment, the coding gene sequence may encode a marker gene product. The term marker gene product is used synonymously with reporter gene product to refer to a gene product whose presence can be readily identified, generally either visually or by conferring cellular resistance to otherwise cytotoxic or cytostatic agents. A number of marker gene products would be known to the person skilled in the art and include, but are not limited to luciferase, green florescent protein, β-galactosidase, □glucuronidase (GUS) and chloramphenicol acetyl transferase (CAT).

Advantageously, in various embodiments, the composition of the present invention will be stable in physiological solutions. The stability may be increased by increasing the stability of the complex formed between the polypeptide and the nucleic acid, for example by increasing the valency of the DNA-binding domains of the polypeptide and DNA sequences recognized by the cognate binding domain. The composition may be formed by mixing the polypeptide and the nucleic acid in an appropriate buffer. The components of the appropriate buffer will depend on the nature of the nucleic acid and polypeptide elements. A person skilled in the art would know to use the appropriate solution conditions to promote the stability of the complex in the composition. For instance, if the binding between the polypeptide and the nucleic acid in the composition is mediated primarily by electrostatic interactions, the person skilled in the art would know to use solutions with relatively low salt concentrations to prevent ionic shielding. The formation of stable non-covalent complexes may be determined by a number of experimental methods that rely on the size and/or charge of the non-covalent complex. For example the complex may be determined by mass spectrometry, gel permeation/size exclusion chromatography, agarose gel electrophoresis, polyacrylamide gel retardation assays, quenching of the fluorescence of ethidium bromide intercalated in DNA, atomic force microscope analysis, zeta potential analysis and dynamic light scattering analysis.

In another embodiment of the present invention, the composition also comprises a cationic polymer. The cationic polymer is believed to interact with the negatively charged backbone of the nucleic acid, causing the non-covalent nucleic acid/polypeptide complex to condense into smaller less negatively charged particles. These smaller less anionic non-covalent complexes may be internalised more efficiently by receptor-mediated endocytosis. (Schaffer et al J. Biol. Hem. 273:28004–28009, 1998). Suitable cationic polymers include protamine, polylysine, polyarginine, polyornitine, polyethylenimine or basic peptide sequences derived from basic proteins such as histones. Preferably the polyethylenimine is a low molecular weight polymer, preferably with an average molecular weight (by weight) of 600 (PEI600). PEI600 is different from higher molecular weight PEI, such as PE125K that displays high toxicity and efficiency of gene trasfection (Boussif O, et al., Proc. Natl. Acad. Sci. USA 92: 7297–7302, 1995; Abdallah B, et al., Hum Gene Ther, 7: 1947–1954, 1996; Goula D, Gene Therapy, 5:712–717 1998). PEI 600 displays much lower cytotoxicity but almost no transfection efficiency. As PEI600 contains 1°, 2° and 3° amines, each with the potential to be protonated, after being incorporated into a complex and endocytosed into cells, the polymer disrupts endosome membranes and promote the escape or release of the polypeptide complex.

The invention also provides a method for targeted delivery of nucleic acids into a cell and comprises administering a composition according to various embodiments of the invention to cells expressing neurotrophin receptors. Without being limited to any particular theory, it is believed that the polypeptide-nucleic acid complex selectively binds to the cell surface neurotrophin receptor, and the complex is then internalized by receptor mediated endocytosis.

Any cell that expresses at least one neurotrophin receptor can be targeted, including cells that express Trk such as Trk A, TrK B and Trk C or $p75^{NTR}$. Among various neuronal cells, these include basal forebrain-cholinergic neurons, striatal-cholinergic neurons, locas ceruleus neurons, spinal cord motor neurons, sympathetic sensory neurons, neural crest-derived small-, medium-, and large-fibre sensory neurons, retinal ganglion cells and others. Other cells in the nervous system include astroglial cells, oligodendrocytes, Schwann cells, microglia, and neuroectoderm-derived cells. Cells outside the nervous system include B lymphocytes, T lymphocytes, mast cells, monocytes, macrophages and many tumor cells.

The composition may comprise other non-viral gene carriers including cationic polymers or lipids described by Davis M E, (Non-viral gene delivery system; Current opinion in biotechnology 2002, 13: 128–131), Niidome T and Huang L (Gene therapy progress and prospects: nonviral vectors. Gene Therapy, 2002, 9:1647–1652) and Li S and Huang L (nonviral gene therapy: promises and challenges. Gene Therapy, 2000, 7:31–34). The polypeptides may also be used in the context of viral vectors after chemical conjugation or replacement of endogenous viral ligands. Retrovirus-mediated gene delivery for use as gene therapy has been well characterized and protocols for producing recombinant retroviruses and for infecting cells in vitro or in vivo with such viruses can be found in Current Protocols in Molecular Biology, Ausubel, F. M. et al. (eds.) Greene Publishing Associates, (1989), and other standard laboratory manuals. Other known viral vectors for gene therapy include adenovirus, adeno-associated viruses and baculovirus-derived vector (Sarkis C et al, Proc Natl Acad Sci U.S.A. 97:14638–43, 2000), including for DNA delivery to cells of the nervous system as described in U.S. Pat. No. 6,180,613.

High-level and cell-specific gene expression is required to effectively treat many neurological disorders by gene therapy. The polypeptides of the present invention may therefore be advantageously used in gene therapy to treat neuronal disorders, including stroke, ischemia, epilepsy, head and spinal cord trauma, Parkinson's diseases, Huntington's disease, Alzheimer's disease, amyotrophic lateral sclerosis, and neurogenetic disorders. For example, in Parkinson's disease, a progressive loss of dopaminergic neurons in the substantia nigra ultimately results in a dopamine deficiency and associated motor impairments. A gene delivery system that targets Trk B receptors expressed on the membrane surface of this group of neurons should be useful for advancing gene therapy for Parkinson's disease. Also in Alzheimer's disease, the group of neurons with the most prominent pathological changes are basal forebrain cholinergic neurons that respond to all neurotrophins. A gene delivery system that targets neurotrophin receptors may help to transfer therapeutic genes into the neurons to augment cholinergic functions. Therapeutic genes that can be used include growth factor genes (which include genes encoding neutrophins, proteins in the fibroblast growth factor family, proteins in the insulin-like growth factor family), and anti-apoptotic genes (including genes of bc1-2 gene family).

The invention in another aspect therefore also provides a method of treating a neuronal disorder in a subject comprising administering to the subject a composition according to various embodiments of the invention. The subject may be any mammal, and in one embodiment, the subject is a human. In various embodiments, the neuronal disorder is stroke, ischemia, epilepsy, head and spinal chord trauma, Parkinson disease, Huntington's disease, Alzheimer's disease, or amyotrophic lateral schlerosis, or a neurological disorder. As will be apparent to a skilled person, the composition can be suitably prepared for in vivo administration using pharmaceutically acceptable carrier or diluent.

Methods for introducing DNA into mammalian cells in vivo are known and may be used to administer DNA complexed with polypeptides of the invention to a subject for gene therapy. In one embodiment, the target cells are neuronal cells and the composition is administered by intrathecal injection into the cerebrospinal fluid (CSF). To deliver the composition specifically to neuronal cells in a particular region of the central nervous system, it may be administered by stereotactic microinjection to a specific anatomical region, as is known in the art. For human patients, the stereotactic frame base will be fixed into the skull and the brain imaged using high resolution MRI. Using appropriate stereotactic software, the images will be translated into 3-dimensional coordinates appropriate for targeted injection of DNA. Sterotactic injection of DNA complexed with polypeptides of the invention into a specific anatomical region will also help to target a specific subtype of neurons at a remote region through retrograde axonal transport. It is also possible to take advantage of retrograde axonal transport to target neurons in the CNS after peripheral injection of the composition. One example is muscular injection to target motor neurons in the spinal cord. The approach bypasses the blood-bran barrier and provides a practical therapeutic strategy that is non-invasive to CNS tissues.

The polypeptides and compositions of the invention have been tested for neurotrophin-like activities and targeted gene delivery in PC12 cells that express Trk A and $p75^{NTR}$, as well as rat primary cortex neurons that express Trk A and Trk B.

The polypeptides improved transfected gene expression by several hundred to several thousand-fold. The specificity of the compositions to target neurotrophin receptors has been confirmed in inhibition experiments using neurotrophins or related control peptides as competitive inhibitors. Furthermore, improved gene delivery using the polypeptides of the invention has been demonstrated in the nervous system after intralumbar injection. Significantly increased gene expression was observed in the dorsal root ganglia, a region expressing neutrophin receptors. Notably, DNA complexed with polypeptides comprising $(SPKR)_4$ and a $His_{10}$ tag may efficiently transfer cells in vitro and in vivo without the use of agents that help endosome escape, such as chloroquine and PEI.

The polypeptides also activate neurotrophin receptor-related signal transduction and exert neurotrophin-like biological effects in promoting neurite outgrowth and neuronal survival. The hairpin motif is therefore a neurotrophin agonist, meaning that it is capable of promoting at least one of the biological effects associated with neurotrophins, such as neurite outgrowth, neuronal survival and neurotrophin receptor-related signal transduction. In one aspect therefore, the invention provides a neurotrophin agonist comprising a hairpin motif that selectively binds to a neurotrophin receptor. The harpin motif may be a hairpin motif of a neurotrophin of a functional equivalent thereof as described above. In one embodiment, the agonist further comprises a positively charged domain and in various other embodiments, comprise other elements, including those described above, for example a suitable linker/spacer between the hairpin motif and the positively charged domain or other elements that enhance the stability, solubility or folding of the agonist.

Without being limited to any particular theory, it is believed that the positively charged domain promotes receptor binding of the agonist by binding to negatively charged cell membrane. The positively charged domain may be any positively charged polymer of amino acids as described above and includes poly-lysine and $SPKR_4$ domain. In various embodiments, the agonist comprises the sequence of SEQ ID NO:5, SEQ ID NO:6, SEQ ID NO:7 and SEQ ID NO:8.

The neurotrophin agonist according to various embodiments of the invention has many uses, as will be readily apparent to a skilled person, including in the study of neurotrophin receptor function. It may also be used in the treatment of disorders responsive to neurotrophin treatment, for example, tumour or neuronal disorders including the aforementioned disorders. The invention therefore also provides a method of treating a disorder responsive to neurotrophin in a subject comprising administering to the subject an effective amount of neurotrophin agonist of the present invention or a composition comprising an effective amount of a neurotrophin agonist of the present invention. The subject may be any mammal including a human.

Another aspect of the invention provides a composition comprising a neutrophin agonist and a pharmaceutically acceptable diluent or carrier. The composition may be manufactured in a conventional manner. In general, a diluent or carrier is selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF. Formulations can be prepared to contain an effective amount (meaning the amount sufficient to effect treatment of a disorder or a symptom thereof), for example, a suitable daily dose. The effective amount and suitable daily dose will vary depending on the subject to be treated and the disorder and its severity and may be routinely determined by one skilled in the art. The effective amount and suitable formulation can be similar to that used in neurotrophin treatment, as described, for example, in R T Thorne and W H Frey: "Delivery of neurotrophin factor to the central nervous system: Pharmacokinetic considerations" in *Clin. Pharmacokinet*, 40(12): 907–946, 2001. In one embodimen, the effective amount is about 0.03 to 1 μg of the agonist per kg of body weight of the subject to be treated if administered by injection.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

The word "comprising" is used as an open-ended term, substantially equivalent to the phrase "including, but not limited to". The phrase "according to the invention" or "according to various embodiments of the invention" is intended to include all embodiments within the scope of the invention. The following examples are illustrative of various aspects of the invention, and do not limit the broad aspects of the invention as disclosed herein.

EXAMPLES

Materials and Methods

Polypeptide Production

Cell Lines

A PC12 (rat pheochromocytoma) cell line was obtained from ATCC (American Type Culture Collection, Manassas, Va., USA) and cultured in RPMI-1640 medium supplemented with 10% fetal bovine serum (FBS) and 5% horse serum. PC12 cells are known to express TrkA and $p75^{NTR}$ receptors. A COS7 (African green monkey kidney fibroblast) cell line was obtained from ATCC and cultured in Dulbecco's modified Eagle's medium (DMEM) supplemented with 10% fetal bovine serum, 50 U/ml penicillin, and 50 μg/ml streptomycin. The cells were maintained in a 37° C., 5% $CO_2$, humidified incubator.

Primary Cell Cultures

Primary cultures of neurons were established from the cortices of embryonic Wistar rats at gestational day 20. Cortices freed of meninges were dissected and individual cells were dispersed mechanically by trituration of minced tissue in 3 ml DMEM medium supplemented with 2% FBS. The suspension was allowed to settle in a centrifuge tube. The cells in the supernatant were collected by centrifugation and resuspended gently in DMEM with 10% FBS. Viability of the cells was assessed prior to plating using trypan blue. Cells were plated onto microplates pre-coated with poly-L-lysine/laminin at a density of $7.5 \times 10^5$ viable cells/cm$^2$. After a two-hour incubation period to allow neurons to attach, the medium and unattached cells were removed and replaced by serum-free DMEM/F12 medium with 1% N2 supplement (Invitrogen, Carlsbad, Calif., USA). The cell were then incubated at 37° C. in 5% $CO_2$ in a humidified incubator. After 2–5 days of culture, the neuron cells were used for transfection experiments.

Primary cultures of glial cells were established from the cortices of 20-day old embryonic Wistar rats. Individual cells were collected as described above. The cells were plated at a density of $4 \times 10^5$ viable cells/$cm^2$ on poly-L-lysine/laminin coated dishes and grown to confluence for 7 days in DMEM/F12 medium supplemented with 10% FCS. The day before transfection, the cells were detached and plated into coated microplates at a density of $2.5 \times 10^4$ cells per well.

N/P Ratio

The1 nitrogen/phosphate (N/P) ratio is a commonly used measure of the charge balance in a polycation-nucleic acid or polypeptide-nucleic acid complex. For cationic polymers, this refers to the ratio of nitrogen atoms in the polycations to the phosphate groups in the nucleic acids. For the purposes of calculating the N/P ratio for our polypeptides, we take the number of basic amino acid residues in the DNA-binding domain to be the number of "N" moieties per polypeptide molecule.

DNA Retardation Assay

This assay qualitatively assesses the ability of a polypeptide or polycation to bind to DNA and thus to retard its migration (by decreasing its charge/mass ratio) through an agarose gel under electrophoresis. For a range of N/P ratios, polypeptide was added to 0.1 μg of plasmid DNA made up to 20 μl with either HEPES-buffered saline (HBS, 150 mM NaCl, 29 mM HEPES, pH 7.3) or 5% glucose. The mixtures were vortexed and incubated at room temperature for 30 minutes before being subjected to electrophoresis in a 0.8–1.0% Tris-borate-EDTA agarose gel stained with ethidium bromide for visualization under ultraviolet light.

Ethidium Bromide Displacement Assay

In this assay, the quenching of the fluorescence of ethidium bromide intercalated in DNA is used to measure DNA-binding and condensing ability. Ethidium bromide (153 μl of a 0.01% solution) was added to 96 μg of plasmid DNA and diluted with water to a final volume of 6 ml. In wells of a 96-well microplate, various amounts of polypeptide were placed in a volume of 50 μl, to which 50 μl of the DNA-ethidium bromide solution was added. After five minutes of mixing, 100 μl of water was added. The fluorescence reading was taken using wavelengths of 485 nm for excitation and 593 nm for emission on a SPECTRAFluor Plus microplate reader (TECAN, Maennedorf, Switzerland).

Atomic Force Microscopy

DNA samples, polypeptide-DNA complexes, and polypeptide-polycation-DNA complexes were prepared with a DNA concentration of 0.02 mg/ml. The samples were diluted ten-fold in HPLC-grade water, and 20 μl of each sample was deposited onto mica discs. After one minute, the mica discs were washed with HPLC-grade water and dried in a stream of filtered air. Images were acquired on a Nanoscope IIIa atomic force microscope (Digital Instruments, Santa Barbara, Calif., USA) operating in tapping mode in air, using Nanoprobe Silicon tips (Digital Instruments).

Reporter Gene Plasmid

To determine the transfection efficiencies of our nucleic acid delivery systems, we employ a reporter plasmid, pCA-Gluc (a gift from Yoshiharu Matsuura, National Institute of Infectious Diseases, Tokyo, Japan), encoding firefly luciferase under the control of the composite promoter, CAG. CAG comprises the chicken β-actin promoter and the cytomegalovirus immediate early enhancer.

Gene Delivery in Vitro

TrkA-targeting gene delivery complexes were tested for transfection efficiency in vitro in PC12 (TrkA and $p75^{NTR}$ positive) cells and COS7 (neurotrophin receptor negative) cells. The cells were grown to 50–70% confluency in microplate wells (24-, 48-, or 96-well plates). The gene delivery complexes were prepared according to specifications presented for each example. Transfection was accomplished by replacing the serum-enriched medium with half the usual volume of reduced-serum medium, Opti-MEM (Invitrogen), containing the gene delivery complexes. Where specifically mentioned, 100 μM of chloroquine was also added to help the complexes escape from endosomes. After four hours of incubation, the cells were restored to the normal medium volume and serum concentration, either by topping up with medium containing twice the usual serum concentration (RPMI-1640 with 20% FBS and 10% horse serum for PC12) or by completely replacing the medium.

Gene delivery complexes were also tested on primary cultures of cortical neurons and glial cells in a similar fashion. However, since the DMEM-F12/N2 medium the neurons are cultured in does not contain serum, the complexes were simply added directly to an amount of DMEM-F12/N2 to make up half the usual volume. Four hours later, an equal volume of DMEM-F12/N2 was added.

One to two days after transfection, the cell culture medium was removed and the cells were rinsed in phosphate-buffered saline (PBS). Enough Reporter Lysis Buffer (Promega, Wisconsin, Md., USA) to cover the bottom surface was added to each well (50 μl/well for 48-well plates). After one freeze-thaw cycle, the lysates were tested for luciferase activity using the Luciferase Assay System (Promega) and a single-tube luminometer (Berthold Lumat L B 9507, Bad Wildbad, Germany). The total protein concentration of each lysate was determined using the DC Protein assay (Bio-Rad, Hercules, Calif., USA). The results were expressed in relative light units (RLU) per milligram of total protein.

Gene Delivery In Vivo

In vivo gene delivery was studied by intrathecal injections of adult Wistar rats (8 weeks old, 180–200 g). The rats were anesthetized by intraperitoneal injection of sodium pentobarbital. After the skin around L4–L5 was exposed, the gene delivery complex was slowly injected into the subarachnoid space using a syringe. A slight tail movement accompanied correct placement of the needle. After injection, the syringe was left in place for five minutes to limit diffusion caused by backflow pressure. Multiple injections were sometimes required to deliver the full volume of the complex. After injection, the skin was closed with surgical clips and the animals were kept warm until they recovered.

After two days, the rats were anesthetized and perfused transcardially with PBS. The lumbar segment of the spinal cord and the lumbar dorsal root ganglia were excised. The tissues were homogenized in 100–400 μl of Reporter Lysis Buffer (Promega) depending on size and subjected to three freeze-thaw cycles. The lysates were centrifuged at 14000 g for 5 min at 4° C. The supernatant was tested for luciferase activity using the Luciferase Assay System (Promega) in a single-tube luminometer (Berthold Lumat LB 9507). The readings were normalized by the total protein content of the lysates, as measured by the DC Protein assay (Bio-Rad).

Detection of TrkA and Signal Transduction Pathway Activation

Immunoblotting experiments were conducted to test whether the chimeric polypeptides could, like NGF, induce autophosphorylation of TrkA and activation of its signal transduction pathways. PC12 cells were seeded in 6-well plates at a density of $2 \times 10^6$ cells/well and cultured in RPMI 1640 containing 0.5% FBS and 0.25% horse serum for 2 days. The low serum concentrations were necessary to reduce the basal levels of phosphorylation. The medium was refreshed two hours before beginning treatment. The cells were incubated with the polypeptides or NGF in serum-free medium for 15–20 min. The cells were then washed in PBS, lysed, and sonicated. The cell lysates were resolved by SDS-PAGE and transferred to a nitrocellulose membrane for immunoblotting. The primary antibodies used include Phospho-TrkA (Tyr490) antibody, Phospho-p44/p42 MAPK (Thr202/Tyr204) monoclonal antibody, and Phospho-Akt (Ser473) monoclonal antibody, all obtained from Cell Signaling Technology (Beverly, Mass., USA). Colorimetric detection was performed by standard techniques after using horse-radish peroxidase-conjugated secondary antibodies. In some experiments, TrkA tyrosine kinase inhibitors K-252a or AG879 (both from Calbiochem, La Jolla, Calif., USA) were used. In these cases, PC12 cells were incubated with 100 nM K-252a or 10 µM AG879 before addition of polypeptides or NGF.

PC12 Cell Survival Assay

Undifferentiated or differentiated (by 6-day treatment with 10 ng/ml NGF) PC12 cells seeded onto collagen-coated 96-well plates were exposed to serum-free RPMI-1640 medium containing either NGF or various concentrations of chimeric polypeptides. After 3–4 days of incubation, cell viability was measured by the standard MTT assay. Cell survival was expressed as a percentage of the viability of the NGF-treated control.

PC12 Neurite Outgrowth Assay

Chimeric polypeptides were examined for their ability to induce neurite outgrowth in PC12 cells. Polypeptides in a range of concentrations were added to PC12 cells cultured in serum-enriched RPMI-1640 medium. The cells were incubated for three days and photographed every 24 h.

Example 1

Design of NL4-10K

NL4-10K comprises loop 4 of NGF and the flanking β-sheet sequences (NL4, amino acids 80–108) linked to a C-terminal nucleic acid binding domain of ten consecutive lysine residues (10K). The first and last amino acid residues of NL4 are cysteine residues, which form an intramolecular disulfide bond to stabilize the loop structure of the TrkA-binding region. The amino acid sequences of NL4-10K, NL4, and 10K are listed as SEQ ID NOS:5, 9 and 10), respectively.

Peptide Synthesis

NL4-10K, NL4, and 10K were chemically synthesized by conventional peptide synthesis techniques. NL4-10K and NL4 were synthesized, cyclized, and purified by Cambridge Research Biochemicals (Cleveland, UK). 10K was obtained from Bio-Synthesis (Lewisville, Tex., USA).

NL4-10K binds DNA

The ability of NL4-10K peptide to bind to DNA was monitored by DNA retardation during electrophoresis. Binding of NL4-10K to plasmid DNA reduces the charge-to-mass ratio of the DNA. FIG. 1 shows that the mobility of plasmid DNA was reduced with increasing peptide concentration. Between the N/P ratios of 1 and 5, the complex became immobile, indicating complete charge neutralization of the DNA. In contrast, NL4, which does not contain a DNA-binding domain, does not retard DNA migration.

NL4-10K Mediates Gene Delivery to PC12 Cells

To examine the efficacy of NL4-10K as a gene delivery vector, complexes formed by self-assembly of the peptide and the reporter plasmid, pCAGluc, at different ratios were used to transfect PC12 cells. The complexes were made by adding peptide drop-wise to DNA while vortexing, with both components dissolved in Opti-MEM medium. Complex formation was allowed to proceed for 30 min at room temperature before transfection. To each well of a 24-well plate, 50 μl of complex was added, containing 1 μg of plasmid DNA. Since NL4-10K lacks an endosome-disrupting domain, chloroquine (100 μM) was used during transfection.

FIG. 2A shows that complexes formed by 0.3 nmol of NL4-10K with 1 μg of pCAGluc (N/P ratio of 1) resulted in modest gene delivery, but the transfection efficiency increased markedly with an increasing amount of NL4-10K. Neither NL4 (targeting domain only) nor 10K (DNA-binding domain only) nor a mixture of the two exhibited this dose-responsive trend. With 1.5 nmol of NL4–01K per μg of DNA (N/P ratio of 5), transfection was 110 times more efficient than that achieved with a mixture of NL4 and 10K peptides.

NL4-10K-Mediated Gene Delivery to PC12 Cells is Specific

For further evidence that NL4-10K-mediated gene delivery is specifically targeted to NGF receptors, a competitive assay was carried out using excess NGF, NL4, and NL4-10K to compete with NL4-10K/pCAGluc complexes for access to TrkA. The presence of each of these molecules during transfection reduced the efficiency of gene delivery by 74–90% (FIG. 2B). The presence of excess 10K peptide, however, did not have a significant effect. These results suggest that NL4-10K-mediated gene delivery to PC12 cells is NGF receptor-specific.

NL4-10K Mediates Gene Delivery to Primary Cultures of Neurons and Glial Cells.

TrkA expression in cortical neurons is well-established, whereas in glial cells, the presence of TrkA is still a matter of contention (Sofroniew at al., Annu. Rev. Neurosci. 2001; 24: 1217–281). If present at all, TrkA is expressed in a small percentage of glial cells and at low levels. We examined the ability of NL4-10K to deliver pCAGluc plasmid to primary cultures of neuronal and glial cells isolated from 20-day old embryonic rats.

Complexes formed at peptide/DNA (nmol/μg) ratio of 0.75 (N/P ratio of 2.5) by self-assembly of NL4-10K and reporter plasmid pCAGLuc were used to transfect both primary neurons and glial cells. FIG. 2C shows that in the presence of chloroquine, NL4-10K peptide/pCAGLuci complexes were 22-fold more efficient than the non-targeted control in gene transfer to primary neurons. In primary glial cells, however, the difference between the transfection efficiencies of NL4-10K and 10K is not significant.

NL4-10K Mediates Gene Delivery to Dorsal Root Ganglia

Neurons of the dorsal root ganglia (DRG) are known to express TrkA. Intralumbar injections of gene delivery complexes were performed on rats to assess the efficacy of NL4-10K in vivo. Chloroquine had been used in vitro to help NL4-10K/DNA complexes escape from endosomes, but it is not useful in vivo because the concentrations required would be toxic. Hence, we added the polycation, low molecular weight polyethylenimine (MW 600 Da, PEI600), to the peptide-DNA complexes for its endosome-disrupting ability and its low toxicity. In forming these triple complexes, PEI600 was first mixed with DNA for 30 min, after which the peptide was added and the mixture incubated for another 30 min at room temperature. Each rat was injected with 60 μl of complex containing 3 μg of pCAGluc, PEI600 at an N/P ratio of 5, and peptide (either NL4-10K or the 10K control) at an N/P ratio of 5, dissolved in 5% glucose. The lumbar segments of the spinal cord and the DRG were collected three days later and assayed for luciferase activity. In the spinal cord near the lumbar injection site, transfection mediated by NL4-10K was decreased relative to the 10K control. In contrast, luciferase gene expression in the DRG resulting from PEI600/pCAGluc/NL4-10K was twice as high as that mediated by PEI600/pCAGluc/10K (FIG. 3). These results demonstrate the specific nature of NL4-10K-enhanced gene delivery in vivo.

Example 2

2.1 Design of DsbC-NL4-10K Recombinant Protein

In comparison to recombinantly produced proteins, peptide synthesis by chemical methods is expensive and faces chain-length limitations. We wish to show that the amino acid sequence of NL4-10K, when incorporated into a recombinant protein, retains its ability to mediate TrkA-targeted gene delivery. The chimeric protein DsbC-NL4-10K (SEQ ID NO:6) consists of NL4-10K attached to the C-terminus of DsbC, an *E. coli* disulfide bond isomerase that should enhance protein stability, solubility, and folding.

Plasmid Construction

The DNA sequence coding for NL4 was PCR-amplified from a pcDNA3.1/GS plasmid containing the NGF gene (Invitrogen H-X52599M), using primers D1-a (SEQ ID NO:12) and D1-b (SEQ ID NO:13). The downstream primer, D1-b, includes in-frame codons for the 10K tail. This sequence was inserted in-frame into pET-40b(+) (Invitrogen) between the ScaI and HindIII sites, downstream of the coding sequences for DsbC and a $His_6$ tag. The sequence of the construct (D1-c: SEQ ID NO:14) was confirmed by conventional DNA sequencing techniques.

Protein Expression and Purification pET-40b(+)-NL4-10K was transformed into the *E. coli* expression host strain BL21(DE3). A single colony of freshly transformed bacteria was suspended in 200 μl of water, re-plated, and incubated overnight. The resulting colonies were pooled and used to inoculate 400 ml of Luria-Bertani (LB) medium containing 30 μg/ml of kanamycin. After rapid shaking at 30° C. for 5 h, the cells were harvested and lysed in 20 mM $Na_2HPO_4$, 0.5 M NaCl, 10 mM imidazole, pH 7.9 containing 1 mg/ml of hen-egg lysozyme for 30 min on ice. After sonication and centrifugation, the supernatant was purified by nickel-chelate affinity chromatography on an ÄKTAexplorer FPLC (Amersham Biosciences, Buckinghamshire, UK). A 1 ml HisTrap column (Amersham Biosciences) was used; washing and eluting was performed by increasing imidazole concentration. The fractions containing purified protein were pooled and dialyzed against HBS at 4° C.

DsbC-NL4-10K Enhances Protamine-Mediated Gene Delivery to PC12 but not COS7 Cells DsbC-NL4-10K binds to DNA but cannot fully condense it because of the bulky DsbC domain. However, in combination with protamine, an arginine-rich basic protein, DsbC-NL4-10K is able to target gene delivery to TrkA receptors. PC12 and COS7 cells grown in 96-well plates were transfected with triple complexes containing 0.1 μg/well of pCAGluc, 0.2 μg/well of protamine, and various amounts of DsbC-NL4-10K. To form these triple complexes, protamine was first mixed with DNA for 30 min, after which DsbC-NL4-10K was added and the mixture incubated for another 30 min at room temperature.

In TrkA-expressing PC12 cells, a dose-response trend was displayed with increasing amounts of DsbC-NL4-10K, with maximum transfection efficiency occurring at a protein/DNA (nmol/μg) ratio of 0.3 (=an N/P ratio of 1) (FIG. 4A). At higher protein/DNA ratios, excess, unbound DsbC-NL4-10K might have given rise to competitive inhibition or toxicity effects. However, in COS7 cells, DsbC-NL4-10K did not improve gene delivery (FIG. 4B), suggesting that the enhancement effect in PC12 cells is NGF receptor-specific.

DsbC-NL4-10K Pre-Treatment Inhibits DsbC-NL4-10K/DNA/PEI600 Transfection

To obtain further evidence of the specific nature of gene delivery mediated by DsbC-NL4-10K, PC12 cells were incubated with free DsbC-NL4-10K 30 minutes before transfection. This pre-treatment greatly reduced the transfection efficiency of DsbC-NL4-10K/DNA/PEI600 complexes, as compared to in cells pre-treated with bovine serum albumin (FIG. 4C). In contrast, pre-treatment with DsbC-NL4-10K or bovine serum albumin result in the similar transgene expression when PEI600/DNA complexes are used. This implies that DsbC-NL4-10K-mediated gene delivery occurs through receptor binding, because pre-treatment with free DsbC-NL4-10K saturates the receptors.

Example 3

Design of SPKR$_4$NL1-2

SPKR$_4$NL1-2 (SEQ ID NO:7) is a chimeric protein that contains a DNA-binding domain, SPKRSPKRSPKRSPKR (SEQ ID NO:11), near the N-terminus, linked to a targeting domain including loops 1 and 2 of NGF by an α-helical linker, TYLSEDELKAAEAAFKRHNPT (SEQ ID NO:30). The sequences of the histone H1-derived DNA-binding domain and the linker were first used by Fortunati et al. (Gene Therapy 2000; 7: 1505–15). The linker is flanked by flexible glycine residues and serves to allow independent action of the DNA-binding and targeting domains. The targeting domain comprises a Cys residue followed by aa 17–67 of human NGF, such that a disulfide bridge can form with the Cys residue corresponding to C58 in NGF. Based on the crystal structure of NGF (Wiesmann et al., Nature 1999; 401: 184–8), we judged that such a disulfide bond would help the targeting domain assume the native conformation of loops 1 and 2.

Plasmid Construction

For a prior work (unpublished), we had constructed a DNA fragment encoding (SPKR)$_4$ and the α-helical linker connected with a third domain by a PCR-mediated gene assembly method (Jayaraman & Puccini, BioTechniques 1992; 12(3): 392–8). Essentially, three long oligonucleotides (D2-a, D2-b, D2-c: SEQ ID NOS: 15, 16, 17, respectively) making up the coding strand, two short oligonucleotides that were complementary to the junctions (D2-d, D2-e: SEQ ID NOS:18, 19, respectively) and two end primers (D2-f, D2-g: SEQ ID NOS:20, 21, respectively) were mixed in a single PCR reaction. Using the product as a template, the sequence corresponding to the DNA-binding domain and the linker was amplified by PCR with the primers D2-h and D2-i (SEQ ID NOS:22 and 23). The PCR product was digested with NdeI and BamHI and ligated into the similarly digested pET-16b expression vector (Novagen), downstream of a $His_{10}$ tag, to create pET16-SPKR$_4$linker. The DNA sequence encoding full length NGF was first cloned into a TA vector by PCR amplification of human brain cDNA (from Clontech, Palo Alto, Calif., USA). The DNA sequence corresponding to aa 17–67 of NGF was amplified with primers D2-j and D2-k (SEQ ID NOS:24 and 25). These primers introduced BamHI restriction sites at both ends to enable the digested fragment to be ligated in frame with the α-helical linker sequence. In addition, the forward primer introduced the additional Cys codon mentioned above. The constructs were checked for correct insert orientation and sequenced by conventional methods. The coding sequence is given in SEQ ID NO:26).

Protein Expression and Purification

The *E. coli* strain BL21(DE3)pLysS transformed with pET16-SPKR$_4$NL1-2 was vigorously shaken at 37° C. in LB medium (containing 50 µg/ml of ampicillin and 34 µg/ml of chloramphenicol) until the optical density reached 0.7. Expression of the recombinant protein was then induced at 30° C. by the addition of 1 mM isopropyl-β-d-thiogalactopyranoside (IPTG, Bio-Rad). The bacteria were harvested by centrifugation 90 min later and frozen. The cell pellet was resuspended in lysis buffer (20 mM Tris-HCl pH 7.9, 0.5 M NaCl, 20 mM imidazole) supplemented with EDTA-free protease inhibitor (Calbiochem, San Diego, Calif., USA). The cell lysate was sonicated until no longer viscous and cleared by centrifugation. The supernatant was purified by nickel-chelate affinity chromatography on an ÄKTAexplorer FPLC (Amersham Biosciences). A 1 ml HisTrap column (Amersham Biosciences) equilibrated with lysis buffer was used to purify lysate from 1.6 L of culture; washing and eluting was performed by increasing the imidazole concentration. The fractions containing the purified protein were pooled and dialyzed against distilled water at 4° C.

SPKR$_4$NL1-2 Binds to Plasmid DNA

The DNA-binding activity of SPKR$_4$NL1-2 was assessed in a DNA retardation assay. When mixed with plasmid DNA, SPKR$_4$NL1-2 reduced the mobility of DNA through an agarose gel under electrophoresis, indicating that the peptide had bound to the DNA and reduced its charge/mass ratio (FIG. 5A).

The ability of SPKR$_4$NL1-2 to bind and condense DNA was also characterized by measuring the quenching of fluorescence when intercalated ethidium bromide is displaced. The fluorescence dropped sharply at an N/P ratio of about 10, indicating the amount of SPKR$_4$NL1-2 needed for DNA condensation (FIG. 5B). The results of the ethidium bromide displacement assay and the DNA retardation assay are similar.

However, atomic force microscopy revealed that the peptide only partially condenses plasmid DNA (result not shown). When PEI600 (N/P ratio of 5) is added, compact nanoparticles are formed (FIG. 5D).

SPKR$_4$NL1-2 Enhances Polycation-Mediated Gene Delivery to PC12 Cells

Complexes made from SPKR$_4$NL1-2 and DNA alone had relatively weak transfection efficiencies, but the addition of polycationic polymer to fully condense the DNA created an effective gene delivery system. PEI600 and low molecular weight poly-L-lysine (PLL, MW 1000) were chosen for their DNA-condensing abilities and low background transfection efficiency. In 48-well plates, PC12 cells were transfected with triple complexes containing 0.25 µg of pCAGluc reporter plasmid, either PEI600 or PLL at an N/P ratio of 5, and various amounts of SPKR$_4$NL1-2. The protein was added to the DNA in Opti-MEM medium, incubated for 30 min at room temperature, after which the polycation was added and the mixture incubated for a further 30 min. Chloroquine was also used with the PLL-containing complexes.

FIG. 6A shows that PEI600-mediated gene transfer is enhanced dramatically by increasing the amount of SPKR$_4$NL1-2. Transgene expression using the highest amount of SPKR$_4$NL1-2 tested was 5000-fold higher than with PEI600 alone. Similarly, with PLL-mediated gene delivery, transfection efficiency with the optimal amount of SPKR$_4$NL1-2 was 1000 times higher than without SPKR$_4$NL1-2 (FIG. 6B).

SPKR$_4$NL1-2-Mediated Gene Delivery is NGF Receptor-Specific

To determine if SPKR$_4$NL1-2-mediated gene delivery is TrkA-specific, we studied the effect of adding NGF (200 ng/ml) during transfection with SPKR$_4$NL1-2/DNA/PEI600 complexes. From FIG. 7, we see that the addition of NGF greatly reduces the transfection efficiency of SPKR$_4$NL1-2/DNA/PEI600. However, when SPKR$_4$NL1-2 is replaced with the control synthetic peptide (SPKR)$_4$, NGF pre-treatment has no significant effect. Since NGF is a competitive inhibitor of SPKR$_4$NL1-2-mediated gene delivery, we can conclude that the action of SPKR$_4$NL1-2 is targeted and receptor-specific. Also, the difference between the (SPKR)$_4$ and SPKR$_4$NL1-2 groups indicated a 1400-fold increase in gene expression resulted from the use of a polypeptide containing loop L1 and L2 of NGF.

SPKR$_4$NL1-2 Specifically Mediates Gene Delivery to Primary Neuron Cultures

The effect of SPKR$_4$NL1-2 on PEI600-mediated gene delivery was also tested on primary cultures of TrkA-expressing cortical neurons and TrkA-poor glial cells isolated from 20-day old embryonic rats. Cortical neurons and glial cells in 48-well plates were transfected with SPKR$_4$NL1-2/PEI600/DNA or (SPKR)$_4$/PEI600/DNA complexes containing 0.25 µg/well of pCAGluc and peptide at an N/P ratio of 5. The complexes were made in Opti-MEM medium by adding SPKR$_4$ NL1-2 to the DNA, waiting for 30 min, adding PEI600, and incubating for a further 30 min at room temperature.

FIG. 8 shows that gene delivery by PEI600 alone is negligible in neuronal and glial cells. When the control peptide (SPKR)$_4$ is added to the complexes, the additional DNA-condensing ability enhances transgene expression in both types of cells, although the impact is higher in glia than in neurons. However, triple complexes containing SPKR$_4$NL1-2 were nine times more effective in neurons than (SPKR)$_4$ triple complexes, while there is essentially no difference between SPKR$_4$NL1-2 and (SPKR)$_4$ in glial cells.

SPKR$_4$NL1-2 Mediates Gene Delivery to Dorsal Root Ganglia

To evaluate the efficacy of SPKR$_4$NL1-2-mediated transfection in vivo, gene delivery complexes were injected intrathecally into the lumbar regions of Wistar rats. The complexes were formed in 5% glucose in the order described above and 4 μg of pCAGluc, PEI600 at an N/P ratio of 5, and 32 nmol of peptide in a volume of 20 μl were injected per rat. The lumbar DRG, which contain TrkA-expressing neurons, were dissected three days later and analyzed for luciferase activity. Transgene expression brought about by SPKR$_4$NL1-2/PEI600/pCAGluc complexes was nine times that of the PEI600/pCAGluc control (FIG. 9).

Example 4

Design of SPKR$_4$BL1-2

The design of the chimeric protein SPKR$_4$BL1-2 (SEQ ID NO:8) is analogous to that of SPKR$_4$NL1-2, where the targeting domain has been changed to bind TrkB by incorporating loops 1 and 2 of BDNF instead of NGF. This targeting domain consists of a Cys residue followed by aa 22–74 of human BDNF, such that an intramolecular disulfide bond is formed with C65 of BDNF. The disulfide bond and loop-flanking β-sheets are intended to stabilize the conformations of the receptor-binding loops. The targeting domain at the C-terminus is separated from the (SPKR)$_4$ DNA-binding domain near the N-terminus by an α-helical linker, TYLSEDELKAAEAAFKRHNPT.

Plasmid Construction

During the construction of the plasmid encoding SPKR$_4$NL1-2, an intermediate plasmid, pET16-SPKR$_4$ linker, had been created that contained the coding sequences of the DNA-binding domain and α-helical linker. A unique BamHI restriction site just 3' of the linker sequence allowed the insertion of the targeting domain. Using the primers D3-a and D3-b (SEQ ID NOS:27 and 28), the sequence coding for loops 1 and 2 of BDNF was amplified from a plasmid bearing the BDNF gene cloned from a human brain cDNA library (Clontech). This primer pair introduced BamHI sites at either end for in-frame ligation into pET16-SPKR$_4$linker. The resulting construct was checked for correct insert orientation and sent for sequence confirmation. The coding sequence of pET16-SPKR$_4$BL1-2 is given in SEQ ID NO:29.

Protein Expression and Purification

E. coli strain BL21(DE3)pLysS bearing the pET16-SPKR$_4$BL1-2 plasmid was cultured in LB medium (containing 50 μg/ml of ampicillin and 34 μg/ml of chloramphenicol) at 37° C. in shake flasks until the optical density reached 0.7. The flasks were moved to a room temperature shaker and induced with 1 mM IPTG after waiting 15 min for the flasks to cool. The bacteria was pelleted by centrifugation 90 min later and frozen. The cells were thawed and lysed in one-tenth the culture volume of 50 mM Na$_2$HPO$_4$, 1 M NaCl, 10 mM imidazole, 0.1% Triton X-100, pH 8.0 with EDTA-free protease inhibitors (Roche Applied Science, Penzberg, Germany). The lysate was sonicated until no longer viscous and cleared by centrifugation. SPKR$_4$BL1-2 was purified from the supernatant by nickel-chelate affinity chromatography on an ÄKTAexplorer FPLC (Amersham Biosciences). For 1.6 L of culture, 4 ml of Ni—NTA Superflow (Qiagen, Hilden, Germany) resin was equilibrated in 50 mM Na$_2$HPO$_4$, 0.3 M NaCl, 10 mM imidazole, pH 8.0; washing and eluting was accomplished by raising the imidazole concentration. The fractions containing purified protein were pooled, dialyzed against distilled water at 4° C., and concentrated.

SPKR$_4$BL1-2 Binds and Condenses DNA

The ability of SPKR$_4$BL1-2 to bind DNA was examined by the DNA retardation assay. FIG. 10A shows that at an N/P ratio of 2 (equivalent to 0.8 nmol/ug DNA), SPKR$_4$BL1-2 is able to completely prevent DNA from migrating under electrophoresis. Atomic force microscopy (FIG. 10B–10D) also revealed that at an N/P ratio of 10, SPKR$_4$BL1-2 was capable of condensing plasmid DNA into particles of under 200 nm in diameter.

SPKR$_4$BL1-2 Mediates Gene Delivery to both Cortical Neurons and Glial Cells

There are no commercially available cell lines that express TrkB; therefore, the transfection ability of SPKR$_4$BL1-2 was tested in vitro on primary cultures of cortical neurons and glial cells obtained from 20-day old embroyonic rats. Cortical neurons are well known to express the full-length TrkB receptor. Astroglial cells were long thought to express only the truncated isoform of TrkB, but Climent et al. (Neurosci. Letters 2000; 288: 53–56) have shown that some full length TrkB is also expressed.

Cortical neurons in 48-well plates were transfected with SPKR$_4$BL1-2/PEI600/DNA complexes containing 0.25 μg/well of pCAGluc. The complexes were made in 5% glucose by adding SPKR$_4$BL1-2 to the DNA, waiting for 30 min, adding PEI600, and incubating for a further 30 min at room temperature. With PEI600 fixed at an N/P ratio of 10, increasing the amount of SPKR$_4$BL1-2 dramatically increased the transgene expression, up to 500-fold at the highest ratio used (FIG. 11A). It was also revealed that PEI600 was not required for efficient transfection.

In the experiment on glial cells, triple complexes were not used. 0.25 μg/well of pCAGluc was complexed with either SPKR$_4$BL1-2 or PEI600 (not both). Gene delivery was increasingly efficient when more SPKR$_4$BL1-2 was used, with transgene expression reaching 180 times that of naked DNA and 50 times that of PEI600/DNA (FIG. 11B).

Example 5

5.1 NL4-10K Activates TrkA and its Signaling Pathways

NGF binds to and induces phosphorylation of TrkA, which in turn elicits signaling cascades that give rise to the bioactivity of NGF. Amongst the involved proteins are Erk1 and Erk2, part of the Ras-MAP kinase pathway, and Akt, which plays an important role in cell survival (Sofroniew at al., Annu. Rev. Neurosci. 2001; 24: 1217–281). The activation of TrkA, Erk1, Erk2, and Akt in PC12 cells treated with 5 μM NL4-10K or NL4 for 20 min was detected by immunoblotting with antibodies that specifically recognized the phosphorylated isoforms. As shown in FIG. 12A, treatment with NL4 and NL4-10K induced activation of TrkA, Erk 1 and Erk 2, and Akt. Furthermore, NL4-10K retained its activity when complexed with DNA.

To further assess the hypothesis that NL4 (with or without the 10K addition) acts via TrkA, two inhibitors, K-252a and AG879, were used to block TrkA protein tyrosine kinase activity. As expected, pre-treatment with these inhibitors greatly reduced the extent of NL4- and NL4-10K-induced phosphorylation of Erk1 and Erk2 (FIG. 12B). These biochemical assays demonstrate that NL4 (with or without the 10K domain) can act through TrkA to activate some of the same signal transduction pathways that NGF activates.

5.2 NL4-10K Promotes Cell Survival of Serum-Withdrawn PC12 Cells

One manifestation of the survival-promoting bioactivity of NGF is its ability to promote the survival of PC12 cells grown in serum-free medium, which otherwise results in a loss of cell viability. Differentiated PC12 cells were grown in serum-free medium containing a range of NL4 or NL4-10K concentrations. The cell survival rate, measured by the MTT assay, was compared to the survival rate promoted by NGF (10 ng/ml, optimal concentration). Over a range of concentrations from 0.125 to 2.5 µM, increasing NL4 concentration resulted in increasing cell survival rates from 68–109% of the optimal NGF-promoted survival rates (FIG. 13). A similar dose response was observed for NL4-10K between 0.125 to 5 µM.

5.3 SPKR$_4$NL1-2 Activates TrkA and its Signaling Pathways

PC12 cells in 6-well plates were treated with SPKR$_4$NL1-2 concentrations ranging from 1–8 µM for 15 min. At all these concentrations, SPKR$_4$NL1-2 induced a higher level of Erk1 and Erk2 activation than 8 µM of the (SPKR)$_4$ control peptide (FIG. 14B). To show that the Erk activation occurred specifically through TrkA phosphorylation, cells were pre-treated with the K-252a TrkA tyrosine kinase inhibitor to see if Erk phosphorylation would be reduced. FIG. 14C shows that Erk phosphorylation induced by 8 µM of SPKR$_4$NL1-2 is reduced and eventually eliminated by increasing concentrations of K-252a.

5.4 SPKR$_4$NL1-2 Promotes Neurite Outgrowth in PC12 Cells

In response to NGF, PC12 cells stop proliferating and differentiate into sympathetic neuron-like cells. Within 2–3 days of NGF treatment, cell morphology changes and neurites can be seen projecting from the cells. We tested SPKR$_4$NL1-2 to see if it could also promote neurite outgrowth in PC12 cells. The cells were treated with 8 µM of either (SPKR)$_4$ or SPKR$_4$NL1-2 for 3 days. Comparing the photographs of (SPKR)$_4$-treated cells (FIG. 15A) and SPKR$_4$NL1-2-treated cells (FIG. 15B), it can be seen that SPKR$_4$NL1-2 has NGF-like bioactivity and promotes neurite outgrowth.

5.5 SPKR$_4$NL1-2 Promotes Cell Survival of Serum-Withdrawn PC12 Cells

We also assessed the ability of SPKR$_4$NL1-2 to promote survival of PC12 cells deprived of serum and NGF for 3 days. The addition of SPKR$_4$NL1-2 (8 µM) to the serum-free medium maintained PC12 viability at 80% of the maximum survival rate promoted by 20 ng/ml NGF (FIG. 15C). The survival-promoting effect exhibited a dose-response trend over the range of 2–8 µM of SPKR$_4$NL1-2.

---

SEQUENCE LISTING

<160> NUMBER OF SEQ ID NOS: 31

<210> SEQ ID NO 1
<211> LENGTH: 119
<212> TYPE: PRT
<213> ORGANISM: Nerve growth factor (NGF) from human

<400> SEQUENCE: 1

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg
        115

<210> SEQ ID NO 2
<211> LENGTH: 126
<212> TYPE: PRT
<213> ORGANISM: Brain-derived neurotrophic factor (BDNF) from human

<400> SEQUENCE: 2

His Ser Asp Pro Ala Arg Arg His Ser Asp Pro Ala Arg Arg Gly Glu

-continued

```
                1               5                   10                  15
Leu Ser Val Cys Asp Ser Ile Ser Glu Trp Val Thr Ala Ala Asp Lys
                20                  25                  30

Lys Thr Ala Val Asp Met Ser Gly Gly Thr Val Thr Val Leu Glu Lys
            35                  40                  45

Val Pro Val Ser Lys Gly Gln Leu Lys Gln Tyr Phe Tyr Glu Thr Lys
        50                  55                  60

Cys Asn Pro Met Gly Tyr Thr Lys Glu Gly Cys Arg Gly Ile Asp Lys
65                  70                  75                  80

Arg His Trp Asn Ser Gln Cys Arg Thr Thr Gln Ser Tyr Val Arg Ala
                85                  90                  95

Leu Thr Met Asp Ser Lys Lys Arg Ile Gly Trp Arg Phe Ile Arg Ile
            100                 105                 110

Asp Thr Ser Cys Val Cys Thr Leu Thr Ile Lys Arg Gly Arg
        115                 120                 125
```

<210> SEQ ID NO 3
<211> LENGTH: 119
<212> TYPE: PRT
<213> ORGANISM: Neurotrophin 3 (NT3) from human

<400> SEQUENCE: 3

```
Tyr Ala Glu His Lys Ser His Arg Gly Glu Tyr Ser Val Cys Asp Ser
1               5                   10                  15

Glu Ser Leu Trp Val Thr Asp Lys Ser Ser Ala Ile Asp Ile Arg Gly
                20                  25                  30

His Gln Val Thr Val Leu Gly Glu Ile Lys Thr Gly Asn Ser Pro Val
            35                  40                  45

Lys Gln Tyr Phe Tyr Glu Thr Arg Cys Lys Glu Ala Arg Pro Val Lys
        50                  55                  60

Asn Gly Cys Arg Gly Ile Asp Asp Lys His Trp Asn Ser Gln Cys Lys
65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
        115
```

<210> SEQ ID NO 4
<211> LENGTH: 130
<212> TYPE: PRT
<213> ORGANISM: Neurotrophin 4/5(NT4/5) from human

<400> SEQUENCE: 4

```
Gly Val Ser Glu Thr Ala Pro Ala Ser Arg Arg Gly Glu Leu Ala Val
1               5                   10                  15

Cys Asp Ala Val Ser Gly Trp Val Thr Asp Arg Arg Thr Ala Val Asp
                20                  25                  30

Leu Arg Gly Arg Glu Val Glu Val Leu Gly Glu Val Pro Ala Ala Gly
            35                  40                  45

Gly Ser Pro Leu Arg Gln Tyr Phe Phe Glu Thr Arg Cys Lys Ala Asp
        50                  55                  60

Asn Ala Glu Glu Gly Gly Pro Gly Ala Gly Gly Gly Cys Arg Gly
65                  70                  75                  80

Val Asp Arg Arg His Trp Val Ser Glu Cys Lys Ala Lys Gln Ser Tyr
```

```
                    85                  90                  95
Val Arg Ala Leu Thr Ala Asp Ala Gln Gly Arg Val Gly Trp Arg Trp
                100                 105                 110

Ile Arg Ile Asp Thr Ala Cys Val Cys Thr Leu Leu Ser Arg Thr Gly
            115                 120                 125

Arg Ala
    130

<210> SEQ ID NO 5
<211> LENGTH: 39
<212> TYPE: PRT
<213> ORGANISM: artificial
<220> FEATURE:
<223> OTHER INFORMATION: NL4-10K
<220> FEATURE:
<223> OTHER INFORMATION: residues 1-29 correspond to residues 80-108 of
      nerve growth factor (NGF) and include loop 4 a known receptor
      binding region
<220> FEATURE:
<223> OTHER INFORMATION: C1 and C29 form a disulfide bridge
<220> FEAT

```
Ala Asp Tyr Asn Ala Leu Gly Ile Thr Val Arg Tyr Leu Ala Phe Pro
    130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
                180                 185                 190

Leu Gly Val Gln Leu Gly Val Ser Gly Thr Pro Ala Val Val Leu Ser
                195                 200                 205

Asn Gly Thr Leu Val Pro Gly Tyr Gln Pro Pro Lys Glu Met Lys Glu
    210                 215                 220

Phe Leu Asp Glu His Gln Lys Met Thr Ser Gly Lys Gly Ser Thr Ser
225                 230                 235                 240

Gly Ser Gly His His His His His Ser Ala Gly Leu Val Pro Arg
                245                 250                 255

Gly Ser Cys Thr Thr Thr His Thr Phe Val Lys Ala Leu Thr Met Asp
                260                 265                 270

Gly Lys Gln Ala Ala Trp Arg Phe Ile Arg Ile Asp Thr Ala Cys Lys
    275                 280                 285

Lys Lys Lys Lys Lys Lys Lys Lys
    290                 295

<210> SEQ ID NO 7
<211> LENGTH: 115
<212> TYPE: PRT
<213> ORGANISM: artificial
<220> FEATURE:
<223> OTHER INFORMATION: SPKR4NL1-2
<220> FEATURE:
<223> OTHER INFORMATION: residues 3-12: His10 tag
<220> FEATURE:
<223> OTHER INFORMATION: residues 23-38: (SPKR)4 DNA-binding domain
<220> FEATURE:
<223> OTHER INFORMATION: residues 41-61: alpha-helical linker
<220> FEATURE:
<223> OTHER INFORMATION: residues 65-115 correspond to aa 17-67 of human
      NGF, including loops 1 and 2 and the flanking beta-sheet sequences
<220> FEATURE:
<223> OTHER INFORMATION: C64 and C106 form a disulfide bridge

<400> SEQUENCE: 7

Met Gly His His His His His His His His His Ser Ser Gly His
1               5                   10                  15

Ile Glu Gly Arg His Met Ser Pro Lys Arg Ser Pro Lys Arg Ser Pro
                20                  25                  30

Lys Arg Ser Pro Lys Arg Gly Gly Thr Tyr Leu Ser Glu Asp Glu Leu
            35                  40                  45

Lys Ala Ala Glu Ala Ala Phe Lys Arg His Asn Pro Thr Gly Ser Cys
    50                  55                  60

Ser Val Ser Val Trp Val Gly Asp Lys Thr Thr Ala Thr Asp Ile Lys
65                  70                  75                  80

Gly Lys Glu Val Met Val Leu Gly Glu Val Asn Ile Asn Asn Ser Val
                85                  90                  95

Phe Lys Gln Tyr Phe Phe Glu Thr Lys Cys Arg Asp Pro Asn Pro Val
                100                 105                 110

Asp Ser Gly
    115
```

```
<210> SEQ ID NO 8
<211> LENGTH: 117
<212> TYPE: PRT
<213> ORGANISM: artificial
<220> FEATURE:
<223> OTHER INFORMATION: SPKR4BL1-2
<220> FEATURE:
<223> OTHER INFORMATION: residues 3-12: His10 tag
<220> FEATURE:
<223> OTHER INFORMATION: residues 23-38: (SPKR)4 DNA-binding domain
<220> FEATURE:
<223> OTHER INFORMATION: residues 41-61: alpha-helical linker
<220> FEATURE:
<223> OTHER INFORMATION: residues 65-117 correspond to aa 22-74 of human
      BDNF, including loops 1 and 2 and the flanking beta-sheet
      sequences
<220> FEATURE:
<223> OTHER INFORMATION: C64 and C108 form a disulfide bridge

<400> SEQUENCE: 8

Met Gly His His His His His His His His His Ser Ser Gly His
1               5                   10                  15

Ile Glu Gly Arg His Met Ser Pro Lys Arg Ser Pro Lys Arg Ser Pro
            20                  25                  30

Lys Arg Ser Pro Lys Arg Gly Gly Thr Tyr Leu Ser Glu Asp Glu Leu
        35                  40                  45

Lys Ala Ala Glu Ala Ala Phe Lys Arg His Asn Pro Thr Gly Ser Cys
    50                  55                  60

Ser Ile Ser Glu Trp Val Thr Ala Ala Asp Lys Lys Thr Ala Val Asp
65                  70                  75                  80

Met Ser Gly Gly Thr Val Thr Val Leu Glu Lys Val Pro Val Ser Lys
                85                  90                  95

Gly Gln Leu Lys Gln Tyr Phe Tyr Glu Thr Lys Cys Asn Pro Met Gly
            100                 105                 110

Tyr Thr Lys Glu Gly
        115

<210> SEQ ID NO 9
<211> LENGTH: 29
<212> TYPE: PRT
<213> ORGANISM: Nerve growth factor (NGF) from human

<400> SEQUENCE: 9

Cys Thr Thr Thr His Thr Phe Val Lys Ala Leu Thr Met Asp Gly Lys
1               5                   10                  15

Gln Ala Ala Trp Arg Phe Ile Arg Ile Asp Thr Ala Cys
            20                  25

<210> SEQ ID NO 10
<211> LENGTH: 10
<212> TYPE: PRT
<213> ORGANISM: artificial
<220> FEATURE:
<223> OTHER INFORMATION: artificial sequence: lysine 10

<400> SEQUENCE: 10

Lys Lys Lys Lys Lys Lys Lys Lys Lys Lys
1               5                   10

<210> SEQ ID NO 11
<211> LENGTH: 16
<212> TYPE: PRT
<213> ORGANISM: ARTIFICIAL
<220> FEATURE:
<223> OTHER INFORMATION: artificial sequence: SPKR4
```

<400> SEQUENCE: 11

Ser Pro Lys Arg Ser Pro Lys Arg Ser Pro Lys Arg Ser Pro Lys Arg
1               5                   10                  15

<210> SEQ ID NO 12
<211> LENGTH: 18
<212> TYPE: DNA
<213> ORGANISM: artificial
<220> FEATURE:
<223> OTHER INFORMATION: forward primer for NL4-10K

<400> SEQUENCE: 12
tgtaccacga ctcacacc                                                     18

<210> SEQ ID NO 13
<211> LENGTH: 59
<212> TYPE: DNA
<213> ORGANISM: artificial
<220> FEATURE:
<223> OTHER INFORMATION: reverse primer for NL4-10K

<400> SEQUENCE: 13
gcaagctttc atttttttt ttttttttt ttttttttt tacaggccgt atctatccg          59

<210> SEQ ID NO 14
<211> LENGTH: 894
<212> TYPE: DNA
<213> ORGANISM: artificial
<220> FEATURE:
<223> OTHER INFORMATION: Coding sequence for DsbC-NL4-10K

<400> SEQUENCE: 14
atgaagaaag gttttatgtt gtttactttg ttagcggcgt tttcaggctt tgctcaggct       60
gatgacgcgg caattcaaca aacgttagcc aaaatgggca tcaaaagcag cgatattcag      120
cccgcgcctg tagctggcat gaagacagtt ctgactaaca gcggcgtgtt gtacatcacc      180
gatgatggta acatatcat tcaggggcca atgtatgacg ttagtggcac ggctccggtc       240
aatgtcacca ataagatgct gttaaagcag ttgaatgcgc ttgaaaaaga gatgatcgtt      300
tataaagcgc cgcaggaaaa acacgtcatc accgtgttta ctgatattac ctgtggttac     360
tgccacaaac tgcatgagca atggcagac tacaacgcgc tggggatcac cgtgcgttat      420
cttgctttcc cgcgccaggg gctggacagc gatgcagaga agaaaatgaa agctatctgg     480
tgtgcgaaag ataaaaacaa agcgtttgat gatgtgatgg caggtaaaag cgtcgcacca     540
gccagttgcg acgtggatat tgccgaccat tacgcacttg gcgtccagct tggcgttagc     600
ggtactccgg cagttgtgct gagcaatggc acacttgttc cggttacca gccgccgaaa       660 gagatgaaag aatttctcga cgaacaccaa aaaatgacca gcggtaaagg atcaactagt     720
ggttctggtc atcaccatca ccatcactcc gcgggtctgg tgccacgcgg tagttgtacc     780
acgactcaca cctttgtcaa ggcgctgacc atggatggca agcaggctgc ctggcggttt     840
atccggatag atacggcctg taaaaaaaaa aaaaaaaaa aaaaaaaaaa atga            894

<210> SEQ ID NO 15
<211> LENGTH: 59
<212> TYPE: DNA
<213> ORGANISM: artificial
<220> FEATURE:
<223> OTHER INFORMATION: First of three long oligonucleotides used in
      assembly of a sequence encoding (SPKR)4 and an a-helix linker

```
<400> SEQUENCE: 15
cgcagtacta gtccgaaacg cagcccgaaa cgtagcccaa agcgtagccc gaagcgtgg      59

<210> SEQ ID NO 16
<211> LENGTH: 59
<212> TYPE: DNA
<213> ORGANISM: artificial
<220> FEATURE:
<223> OTHER INFORMATION: Second of three long oligonucleotides used in
      assembly of a sequence encoding (SPKR)4 and an a-helix linker

<400> SEQUENCE: 16
cggtacctac ctgtctgaag atgagctgaa agcggcggag gcggcattca aacgtcaca      59

<210> SEQ ID NO 17
<211> LENGTH: 57
<212> TYPE: DNA
<213> ORGANISM: artificial
<220> FEATURE:
<223> OTHER INFORMATION: Third of three long oligonucleotides used in
      assembly of a sequence encoding (SPKR)4 and an a-helix linker

<400> SEQUENCE: 17
acccgactgg atccggttgt gtgcctgtgt ctaaaggtca actgtgctaa gcttggc        57

<210> SEQ ID NO 18
<211> LENGTH: 20
<212> TYPE: DNA
<213> ORGANISM: artificial
<220> FEATURE:
<223> OTHER INFORMATION: First bridging oligonucleotide used in assembly
      of a sequence encoding (SPKR)4 and an a-helix linker

<400> SEQUENCE: 18
gtaggtaccg ccacgcttcg                                                  20

<210> SEQ ID NO 19
<211> LENGTH: 20
<212> TYPE: DNA
<213> ORGANISM: artificial
<220> FEATURE:
<223> OTHER INFORMATION: Second bridging oligonucleotide used in
      assembly of a sequence encoding (SPKR)4 and an a-helix linker

<400> SEQUENCE: 19
ccagtcgggt tgtgacgttt                                                  20

<210> SEQ ID NO 20
<211> LENGTH: 20
<212> TYPE: DNA
<213> ORGANISM: artificial
<220> FEATURE:
<223> OTHER INFORMATION: artificial primer

<400> SEQUENCE: 20
cgcagtacta gcccgaaacg                                                  20

<210> SEQ ID NO 21
<211> LENGTH: 20
<212> TYPE: DNA
<213> ORGANISM: artificial
<220> FEATURE:
<223> OTHER INFORMATION: artificial primer

<400> SEQUENCE: 21
gccaagctta gcacagttga                                                  20
```

<210> SEQ ID NO 22
<211> LENGTH: 25
<212> TYPE: DNA
<213> ORGANISM: artificial
<220> FEATURE:
<223> OTHER INFORMATION: artificial primer

<400> SEQUENCE: 22
ccagacatat gagtccgaaa cgcag                                          25

<210> SEQ ID NO 23
<211> LENGTH: 20
<212> TYPE: DNA
<213> ORGANISM: artificial
<220> FEATURE:
<223> OTHER INFORMATION: artificial primer

<400> SEQUENCE: 23
ccggatccag tcgggttgtg                                                20

<210> SEQ ID NO 24
<211> LENGTH: 26
<212> TYPE: DNA
<213> ORGANISM: artificial
<220> FEATURE:
<223> OTHER INFORMATION: artificial primer

<400> SEQUENCE: 24
ctggatcctg cagtgtcagc gtgtgg                                         26

<210> SEQ ID NO 25
<211> LENGTH: 24
<212> TYPE: DNA
<213> ORGANISM: artificial
<220> FEATURE:
<223> OTHER INFORMATION: artificial primer

<400> SEQUENCE: 25
atggatcctc acccgctgtc aacg                                           24

<210> SEQ ID NO 26
<211> LENGTH: 348
<212> TYPE: DNA
<213> ORGANISM: artificial
<220> FEATURE:
<223> OTHER INFORMATION: Coding sequence of SPKR4NL1-2

<400> SEQUENCE: 26
atgggccatc atcatcatca tcatcatcat catcacagca gcggccatat cgaaggtcgt     60
catatgagtc cgaaacgcag cccgaaacgt agcccaaagc gtagcccgaa gcgtggcggt    120
acctacctgt ctgaagatga gctgaaagcg gcggaggcgg cattcaaacg tcacaacccg    180
actggatcct gcagtgtcag cgtgtgggtt ggggataaga ccaccgccac agacatcaag    240
ggcaaggagg tgatggtgtt gggagaggtg aacattaaca acagtgtatt caaacagtac    300 tttttttgaga ccaagtgccg ggacccaaat cccgttgaca gcgggtga                348

<210> SEQ ID NO 27
<211> LENGTH: 31
<212> TYPE: DNA
<213> ORGANISM: artificial
<220> FEATURE:
<223> OTHER INFORMATION: artificial primer -continued

<400> SEQUENCE: 27
ctggatcctg cagtattagt gagtgggtaa c 31

<210> SEQ ID NO 28
<211> LENGTH: 29
<212> TYPE: DNA
<213> ORGANISM: artificial
<220> FEATURE:
<223> OTHER INFORMATION: artificial primer

<400> SEQUENCE: 28
atggatcctc agccttcttt tgtgtaacc 29

<210> SEQ ID NO 29
<211> LENGTH: 354
<212> TYPE: DNA
<213> ORGANISM: artificial
<220> FEATURE:
<223> OTHER INFORMATION: Coding sequence for SPKR4BL1-2

<400> SEQUENCE: 29
atgggccatc atcatcatca tcatcatcat catcacagca gcggccatat cgaaggtcgt 60
catatgagtc cgaaacgcag cccgaaacgt agcccaaagc gtagcccgaa gcgtggcggt 120
acctacctgt ctgaagatga gctgaaagcg gcggaggcgg cattcaaacg tcacaacccg 180
actggatcct gcagtattag tgagtgggta acggcggcag acaaaaagac tgcagtggac 240
atgtcgggcg ggacggtcac agtccttgaa aaggtccctg tatcaaaagg ccaactgaag 300
caatacttct acgagaccaa gtgcaatccc atgggttaca caaaagaagg ctga 354

<210> SEQ ID NO 30
<211> LENGTH: 21
<212> TYPE: PRT
<213> ORGANISM: artificial
<220> FEATURE:
<223> OTHER INFORMATION: H1 alpha helix

<400> SEQUENCE: 30

Thr Tyr Leu Ser Glu Asp Glu Leu Lys Ala Ala Glu Ala Ala Phe Lys
1               5                   10                  15

Arg His Asn Pro Thr
            20

<210> SEQ ID NO 31
<211> LENGTH: 120
<212> TYPE: DNA
<213> ORGANISM: artificial
<220> FEATURE:
<223> OTHER INFORMATION: NL4-10K coding sequence

<400> SEQUENCE: 31
tgtaccacga ctcacacctt tgtcaaggcg ctgaccatgg atggcaagca ggctgcctgg 60
cggtttatcc ggatagatac ggcctgtaaa aaaaaaaaaa aaaaaaaaaa aaaaaaatga 120


We claim:

1. A recombinant polypeptide comprising a cell targeting element and a nucleic acid binding element wherein the cell targeting element is a hairpin motif consisting of amino acids 80 to 108 of SEQ ID NO: 1, amino acids 17 to 67 of SEQ ID NO: 1, or amino acids 81 to 107 of SEQ ID NO: 1, and wherein the hairpin motif selectively binds to a neurotrophin receptor.

2. The polyp eptide according to claim 1 wherein the neurotrophin receptor is TrkA, TrkB, TrkC or $p75^{NTR}$.

3. The polypeptide according to claim 2 wherein the receptor is TrkA.

4. The polypeptide according to claim 1 wherein the nucleic acid binding element is a DNA binding element.

5. The polypeptide according to claim 4 wherein the DNA-binding element is a non-specific DNA binding element.

6. The polypeptide according to claim 5 wherein the DNA binding element is positively charged.

7. The polypeptide according to claim 6 wherein the non-specific DNA binding element is a $(SPKR)_4$ domain or poly-L-lysine.

8. The polypeptide according to claim 7 wherein poly-L-lysine is deca-L-lysine.

9. The polypeptide according to claim 7 comprising a cysteine at the amino and the carboxy ends of the hairpin motif.

10. The polypeptide according to claim 9 comprising a linker sequence between the DNA binding element and the cell targeting element.

11. The polypeptide according to claim 1 comprising the sequence of SEQ ID NO:5, SEQ ID NO:6 or SEQ ID NO:7.

12. The polypeptide according to claim 6 which is a neurotrophin agonist.

13. The polypeptide according to claim 12 comprising the sequence of SEQ ID NO:5, SEQ ID NO:6 or SEQ ID NO:7.

14. A composition comprising a nucleic acid and a recombinant polypeptide according to claim 1.

15. The composition according to claim 14 wherein the nucleic acid is DNA.

16. The composition according to claim 15, wherein the DNA comprises a coding gene sequence.

17. The polypeptide according to claim 7 comprising a linker sequence between the DNA binding element and the cell targeting element.

* * * * *